US008715173B2

(12) United States Patent
Berglund et al.

(10) Patent No.: US 8,715,173 B2
(45) Date of Patent: May 6, 2014

(54) OTOSCANNER WITH FAN AND RING LASER

(75) Inventors: Nathanael Berglund, Atlanta, GA (US);
Harris Bergman, Marietta, GA (US);
Scott Cahall, Fairport, NY (US); Jerry Foster, Lawrenceville, GA (US); Eohan George, Atlanta, GA (US); Samuel W. Harris, Norcross, GA (US); Giorgos Hatzilias, Buford, GA (US); Karol Hatzilias, Atlanta, GA (US); Ruizhi Hong, Roswell, GA (US); Wess E. Sharpe, Vinings, GA (US); David G. Stites, Saint Petersburg, FL (US); Harry S. Strothers, IV, Chamblee, GA (US)

(73) Assignee: United Sciences, LLC, Atlanta, GA (US)

( * ) Notice: Subject to any disclaimer, the term of this patent is extended or adjusted under 35 U.S.C. 154(b) by 0 days.

(21) Appl. No.: 13/586,411

(22) Filed: Aug. 15, 2012

(65) Prior Publication Data
US 2013/0237764 A1 Sep. 12, 2013

Related U.S. Application Data

(63) Continuation of application No. 13/417,649, filed on Mar. 12, 2012.

(51) Int. Cl.
*A61B 1/267* (2006.01)
(52) U.S. Cl.
USPC .......................................... 600/200; 600/117
(58) Field of Classification Search
USPC ......... 600/200, 249, 103, 108, 109, 117, 118, 600/131, 160, 178–180, 182; 623/10
See application file for complete search history.

(56) References Cited

U.S. PATENT DOCUMENTS

| | | | | | |
|---|---|---|---|---|---|
| 4,185,918 | A | * | 1/1980 | DiMatteo et al. | 356/610 |
| 4,396,945 | A | * | 8/1983 | DiMatteo et al. | 348/139 |
| 4,434,800 | A | * | 3/1984 | Anson et al. | 600/473 |
| 4,575,805 | A | * | 3/1986 | Moermann et al. | 700/163 |
| 4,585,349 | A | * | 4/1986 | Gross et al. | 356/624 |
| 4,622,967 | A | * | 11/1986 | Schachar | 606/14 |
| 4,637,715 | A | * | 1/1987 | Idesawa | 356/3.16 |
| 4,645,348 | A | * | 2/1987 | Dewar et al. | 356/603 |
| 4,705,401 | A | * | 11/1987 | Addleman et al. | 356/606 |
| 4,774,403 | A | * | 9/1988 | Arts | 250/205 |
| 4,821,117 | A | * | 4/1989 | Sekiguchi | 348/68 |
| 4,885,634 | A | * | 12/1989 | Yabe | 348/71 |
| 4,986,262 | A | * | 1/1991 | Saito | 600/108 |
| 5,044,373 | A | * | 9/1991 | Northeved et al. | 600/559 |

(Continued)

*Primary Examiner* — Pedro Philogene
*Assistant Examiner* — Lynnsy Schneider
(74) *Attorney, Agent, or Firm* — John R. Biggers; H. Artoush Ohanian; Biggers Kennedy Lenart Spraggins LLP

(57) ABSTRACT

An otoscanner including a conical laser-reflective optical element and a laser light source and the conical laser-reflecting optical element are configured so that the conical laser-reflecting optical element, when illuminated by the laser light source, projects a broken ring of laser light upon an interior surface of the ear when the ear probe is positioned in the ear and a diffractive laser optic lens and the laser light source and the diffractive laser optic lens are configured so that the diffractive laser optic lens, when illuminated by the laser light source, projects upon an interior surface of the ear a fan of laser light at a predetermined angle with respect to a front surface of the diffractive laser optic lens when the ear probe is positioned in the ear.

16 Claims, 21 Drawing Sheets

(56) References Cited

U.S. PATENT DOCUMENTS

| | | | | |
|---|---|---|---|---|
| 5,056,204 A * | 10/1991 | Bartschi | ................... | 29/896.21 |
| 5,090,400 A * | 2/1992 | Saito | ................... | 600/108 |
| 5,200,819 A * | 4/1993 | Nudelman et al. | ................... | 348/65 |
| 5,218,427 A * | 6/1993 | Koch | ................... | 356/602 |
| 5,280,378 A * | 1/1994 | Lombardo | ................... | 359/199.1 |
| 5,294,940 A * | 3/1994 | Wennagel et al. | ................... | 345/31 |
| 5,419,312 A * | 5/1995 | Arenberg et al. | ................... | 600/108 |
| 5,432,543 A * | 7/1995 | Hasegawa et al. | ................... | 348/45 |
| 5,436,655 A * | 7/1995 | Hiyama et al. | ................... | 348/45 |
| 5,487,012 A * | 1/1996 | Topholm et al. | ................... | 700/163 |
| 5,546,189 A * | 8/1996 | Svetkoff et al. | ................... | 356/602 |
| 5,605,531 A * | 2/1997 | Lane et al. | ................... | 600/118 |
| 5,702,249 A * | 12/1997 | Cooper | ................... | 433/29 |
| 5,714,832 A * | 2/1998 | Shirrod et al. | ................... | 310/328 |
| 5,733,246 A * | 3/1998 | Forkey | ................... | 600/160 |
| 5,740,802 A * | 4/1998 | Nafis et al. | ................... | 600/407 |
| 5,747,789 A * | 5/1998 | Godik | ................... | 250/208.1 |
| 5,753,931 A * | 5/1998 | Borchers et al. | ................... | 250/559.22 |
| 5,784,098 A * | 7/1998 | Shoji et al. | ................... | 348/45 |
| 5,825,495 A * | 10/1998 | Huber | ................... | 356/600 |
| 5,831,601 A * | 11/1998 | Vogeley et al. | ................... | 345/175 |
| 5,840,017 A * | 11/1998 | Furusawa et al. | ................... | 600/160 |
| 5,847,832 A * | 12/1998 | Liskow et al. | ................... | 356/613 |
| 5,883,385 A * | 3/1999 | Takahashi et al. | ................... | 250/235 |
| 5,891,016 A * | 4/1999 | Utsui et al. | ................... | 600/181 |
| 5,895,927 A * | 4/1999 | Brown | ................... | 250/559.19 |
| 5,897,494 A * | 4/1999 | Flock et al. | ................... | 600/407 |
| 5,926,388 A * | 7/1999 | Kimbrough et al. | ................... | 700/118 |
| 5,936,628 A * | 8/1999 | Kitamura et al. | ................... | 345/420 |
| 5,978,092 A * | 11/1999 | Brown | ................... | 356/608 |
| 6,028,672 A * | 2/2000 | Geng | ................... | 356/602 |
| 6,044,170 A * | 3/2000 | Migdal et al. | ................... | 382/154 |
| 6,069,698 A * | 5/2000 | Ozawa et al. | ................... | 356/511 |
| 6,081,612 A * | 6/2000 | Gutkowicz-Krusin et al. | ................... | 382/128 |
| 6,110,106 A * | 8/2000 | MacKinnon et al. | ................... | 600/181 |
| 6,179,777 B1 * | 1/2001 | Ninomiya et al. | ................... | 600/160 |
| 6,186,944 B1 * | 2/2001 | Tsai | ................... | 600/200 |
| 6,217,510 B1 * | 4/2001 | Ozawa et al. | ................... | 600/129 |
| 6,292,263 B1 * | 9/2001 | Norita et al. | ................... | 356/639 |
| 6,293,911 B1 * | 9/2001 | Imaizumi et al. | ................... | 600/160 |
| 6,327,041 B1 * | 12/2001 | Guern | ................... | 356/601 |
| 6,361,489 B1 * | 3/2002 | Tsai | ................... | 600/109 |
| 6,377,865 B1 * | 4/2002 | Edelsbrunner et al. | ................... | 700/98 |
| 6,383,133 B1 * | 5/2002 | Jones | ................... | 600/200 |
| 6,393,431 B1 * | 5/2002 | Salvati et al. | ................... | 1/1 |
| 6,450,970 B1 * | 9/2002 | Mahler et al. | ................... | 600/549 |
| 6,459,493 B1 * | 10/2002 | Sugiura et al. | ................... | 356/630 |
| 6,470,124 B1 * | 10/2002 | Le Gargasson et al. | ................... | 385/117 |
| 6,471,636 B1 * | 10/2002 | Sano et al. | ................... | 600/109 |
| 6,532,299 B1 * | 3/2003 | Sachdeva et al. | ................... | 382/128 |
| 6,573,513 B2 * | 6/2003 | Hayashi | ................... | 250/458.1 |
| 6,602,186 B1 * | 8/2003 | Sugimoto et al. | ................... | 600/126 |
| 6,603,552 B1 * | 8/2003 | Cline et al. | ................... | 356/417 |
| 6,626,825 B2 * | 9/2003 | Tsai | ................... | 600/109 |
| 6,679,839 B2 * | 1/2004 | Farkas et al. | ................... | 600/178 |
| 6,751,494 B2 * | 6/2004 | Collier et al. | ................... | 600/407 |
| 6,753,966 B2 * | 6/2004 | Von Rosenberg | ................... | 356/432 |
| 6,918,538 B2 * | 7/2005 | Breytman et al. | ................... | 235/454 |
| 6,920,414 B2 * | 7/2005 | Topholm | ................... | 703/1 |
| 6,937,348 B2 * | 8/2005 | Geng | ................... | 356/603 |
| 6,949,069 B2 * | 9/2005 | Farkas et al. | ................... | 600/178 |
| 7,110,124 B2 * | 9/2006 | Jensen et al. | ................... | 356/626 |
| 7,137,948 B2 * | 11/2006 | Tsai | ................... | 600/109 |
| 7,162,323 B2 * | 1/2007 | Brumback et al. | ................... | 700/118 |
| 7,179,222 B2 * | 2/2007 | Imaizumi et al. | ................... | 600/109 |
| 7,206,067 B2 * | 4/2007 | Jensen et al. | ................... | 356/241.1 |
| 7,251,025 B2 * | 7/2007 | Jensen et al. | ................... | 356/241.1 |
| 7,258,663 B2 * | 8/2007 | Doguchi et al. | ................... | 600/109 |
| 7,311,723 B2 * | 12/2007 | Seibel et al. | ................... | 607/89 |
| 7,341,557 B2 * | 3/2008 | Cline et al. | ................... | 600/160 |
| 7,371,218 B2 * | 5/2008 | Walston et al. | ................... | 600/437 |
| 7,399,181 B2 * | 7/2008 | Weber et al. | ................... | 433/29 |
| 7,419,467 B2 * | 9/2008 | Tsai | ................... | 600/109 |
| 7,421,140 B2 * | 9/2008 | Rottem | ................... | 382/254 |
| 7,446,885 B2 * | 11/2008 | Zabolitzky et al. | ................... | 356/601 |
| 7,448,753 B1 * | 11/2008 | Chinnock | ................... | 351/206 |
| 7,490,085 B2 * | 2/2009 | Walker et al. | ................... | 1/1 |
| 7,544,163 B2 * | 6/2009 | MacKinnon et al. | ................... | 600/178 |
| 7,553,020 B2 * | 6/2009 | Goldfain et al. | ................... | 351/206 |
| 7,583,872 B2 * | 9/2009 | Seibel et al. | ................... | 385/25 |
| 7,625,335 B2 * | 12/2009 | Deichmann et al. | ................... | 600/117 |
| 7,722,534 B2 * | 5/2010 | Cline et al. | ................... | 600/160 |
| 7,801,584 B2 * | 9/2010 | Iddan et al. | ................... | 600/407 |
| 7,802,909 B2 * | 9/2010 | Baker | ................... | 362/572 |
| 7,813,591 B2 * | 10/2010 | Paley et al. | ................... | 382/285 |
| 7,835,925 B2 * | 11/2010 | Roe et al. | ................... | 705/3 |
| 7,912,257 B2 * | 3/2011 | Paley et al. | ................... | 382/128 |
| 7,925,333 B2 * | 4/2011 | Weir et al. | ................... | 600/476 |
| 7,937,253 B2 * | 5/2011 | Anast et al. | ................... | 703/6 |
| 7,949,385 B2 * | 5/2011 | Khamene et al. | ................... | 600/416 |
| 7,961,981 B2 * | 6/2011 | Berg | ................... | 382/286 |
| 7,976,474 B2 * | 7/2011 | Zoth et al. | ................... | 600/559 |
| 7,995,214 B2 * | 8/2011 | Forster et al. | ................... | 356/601 |
| 7,996,068 B2 * | 8/2011 | Telischak et al. | ................... | 600/476 |
| 8,035,637 B2 * | 10/2011 | Kriveshko | ................... | 345/419 |
| 8,100,826 B2 * | 1/2012 | MacKinnon et al. | ................... | 600/178 |
| 8,107,086 B2 * | 1/2012 | Hart et al. | ................... | 356/601 |
| 8,112,146 B2 * | 2/2012 | Hart et al. | ................... | 600/476 |
| 8,169,470 B2 * | 5/2012 | Ishihara et al. | ................... | 348/70 |
| 8,206,290 B2 * | 6/2012 | Huang | ................... | 600/200 |
| 8,212,884 B2 * | 7/2012 | Seibel et al. | ................... | 348/220.1 |
| 8,228,368 B2 * | 7/2012 | Zhao et al. | ................... | 348/45 |
| 8,239,001 B2 * | 8/2012 | Verard et al. | ................... | 600/424 |
| 8,249,461 B2 * | 8/2012 | Vaerndal | ................... | 398/118 |
| 8,271,069 B2 * | 9/2012 | Jascob et al. | ................... | 600/424 |
| 8,310,560 B2 * | 11/2012 | Hart et al. | ................... | 348/222.1 |
| 8,319,184 B2 * | 11/2012 | Hart et al. | ................... | 250/361 R |
| 8,328,731 B2 * | 12/2012 | Hessel et al. | ................... | 600/559 |
| 8,384,916 B2 * | 2/2013 | Hart et al. | ................... | 356/625 |
| 2001/0044668 A1 * | 11/2001 | Kimbrough et al. | ................... | 700/118 |
| 2003/0074174 A1 * | 4/2003 | Fu et al. | ................... | 703/13 |
| 2003/0139673 A1 * | 7/2003 | Vivenzio et al. | ................... | 600/490 |
| 2003/0171655 A1 * | 9/2003 | Newman et al. | ................... | 600/200 |
| 2004/0107080 A1 * | 6/2004 | Deichmann et al. | ................... | 703/6 |
| 2004/0122787 A1 * | 6/2004 | Avinash et al. | ................... | 706/50 |
| 2005/0068544 A1 * | 3/2005 | Doemens et al. | ................... | 356/601 |
| 2006/0282009 A1 * | 12/2006 | Oberg et al. | ................... | 600/559 |
| 2007/0112273 A1 * | 5/2007 | Rogers | ................... | 600/475 |
| 2007/0153296 A1 * | 7/2007 | Schick | ................... | 356/609 |
| 2007/0270647 A1 * | 11/2007 | Nahen et al. | ................... | 600/131 |
| 2007/0270788 A1 * | 11/2007 | Nahen et al. | ................... | 606/15 |
| 2008/0045799 A1 * | 2/2008 | Whitehead et al. | ................... | 600/178 |
| 2008/0045800 A2 * | 2/2008 | Farr | ................... | 600/179 |
| 2008/0119693 A1 * | 5/2008 | Makower et al. | ................... | 600/114 |
| 2008/0146915 A1 * | 6/2008 | McMorrow | ................... | 600/424 |
| 2008/0208006 A1 * | 8/2008 | Farr | ................... | 600/178 |
| 2008/0208297 A1 * | 8/2008 | Gertner et al. | ................... | 607/92 |
| 2008/0275483 A1 * | 11/2008 | Makower et al. | ................... | 606/192 |
| 2008/0281156 A1 * | 11/2008 | Makower et al. | ................... | 600/118 |
| 2008/0281167 A1 * | 11/2008 | Soderberg et al. | ................... | 600/300 |
| 2009/0189972 A1 * | 7/2009 | Harris et al. | ................... | 348/14.08 |
| 2009/0221880 A1 * | 9/2009 | Soderberg et al. | ................... | 600/300 |
| 2009/0221920 A1 * | 9/2009 | Boppart et al. | ................... | 600/476 |
| 2009/0292168 A1 * | 11/2009 | Farr | ................... | 600/109 |
| 2009/0312638 A1 * | 12/2009 | Bartlett | ................... | 600/443 |
| 2009/0318758 A1 * | 12/2009 | Farr et al. | ................... | 600/112 |
| 2010/0060718 A1 * | 3/2010 | Forster et al. | ................... | 348/47 |
| 2010/0198009 A1 * | 8/2010 | Farr et al. | ................... | 600/109 |
| 2010/0231513 A1 * | 9/2010 | Deliwala | ................... | 345/158 |
| 2010/0239126 A1 * | 9/2010 | Grafenberg et al. | ................... | 382/106 |
| 2011/0028790 A1 * | 2/2011 | Farr et al. | ................... | 600/187 |
| 2011/0102763 A1 * | 5/2011 | Brown et al. | ................... | 356/4.01 |
| 2011/0130652 A1 * | 6/2011 | Boppart et al. | ................... | 600/425 |
| 2011/0137118 A1 * | 6/2011 | Huang | ................... | 600/109 |
| 2012/0039493 A1 * | 2/2012 | Rucker et al. | ................... | 381/166 |
| 2012/0057734 A1 * | 3/2012 | Ambrose et al. | ................... | 381/328 |
| 2012/0063644 A1 * | 3/2012 | Popovic | ................... | 382/103 |
| 2012/0140301 A1 * | 6/2012 | Xu et al. | ................... | 359/198.1 |
| 2012/0187190 A1 * | 7/2012 | Wang et al. | ................... | 235/462.06 |
| 2012/0281071 A1 * | 11/2012 | Bergman et al. | ................... | 348/46 |
| 2012/0310098 A1 * | 12/2012 | Popovic | ................... | 600/476 |
| 2012/0327287 A1 * | 12/2012 | Meyers et al. | ................... | 348/335 |
| 2012/0327426 A1 * | 12/2012 | Hart et al. | ................... | 356/601 |

(56) References Cited

U.S. PATENT DOCUMENTS

| | | | |
|---|---|---|---|
| 2012/0327427 A1* | 12/2012 | Hart et al. | 356/601 |
| 2013/0002426 A1* | 1/2013 | Hart et al. | 340/540 |
| 2013/0002824 A1* | 1/2013 | Hart et al. | 348/46 |
| 2013/0003078 A1* | 1/2013 | Hart et al. | 356/601 |
| 2013/0027515 A1* | 1/2013 | Vinther et al. | 348/44 |
| 2013/0027516 A1* | 1/2013 | Hart et al. | 348/45 |

* cited by examiner

OTOSCANNER WITH FAN AND RING LASER

CROSS-REFERENCE TO RELATED APPLICATION

This application is a continuation application of and claims priority from U.S. patent application Ser. No. 13/417,649, filed on Mar. 12, 2012.

BACKGROUND OF THE INVENTION

The present invention relates to determining the shape of surfaces of soft tissue, and more specifically, to determining such shapes using optical technology. Hearing aids, hearing protection, and custom head phones often require silicone impressions to be made of a patient's ear canal. Audiologists inject the silicone material into an ear, wait for it to harden, and then provide the mold to manufacturers who use the resulting silicone impression to create a custom fitting in-ear device. The process is slow, expensive, inconsistent, unpleasant for the patient, and can even be dangerous, as injecting silicone risks affecting the ear drum. Also, there are a range of other medical needs that benefit from determining the shape of body surfaces, including surfaces defining body orifices, such as the size of shape of an ear canal, throat, mouth, nostrils, or intestines of a patient. For example, surgery may be guided by knowing such shapes or medical devices fashioned to have a custom fit for such shapes.

DETAILED DESCRIPTION OF EXAMPLE EMBODIMENTS

Figure 1A:
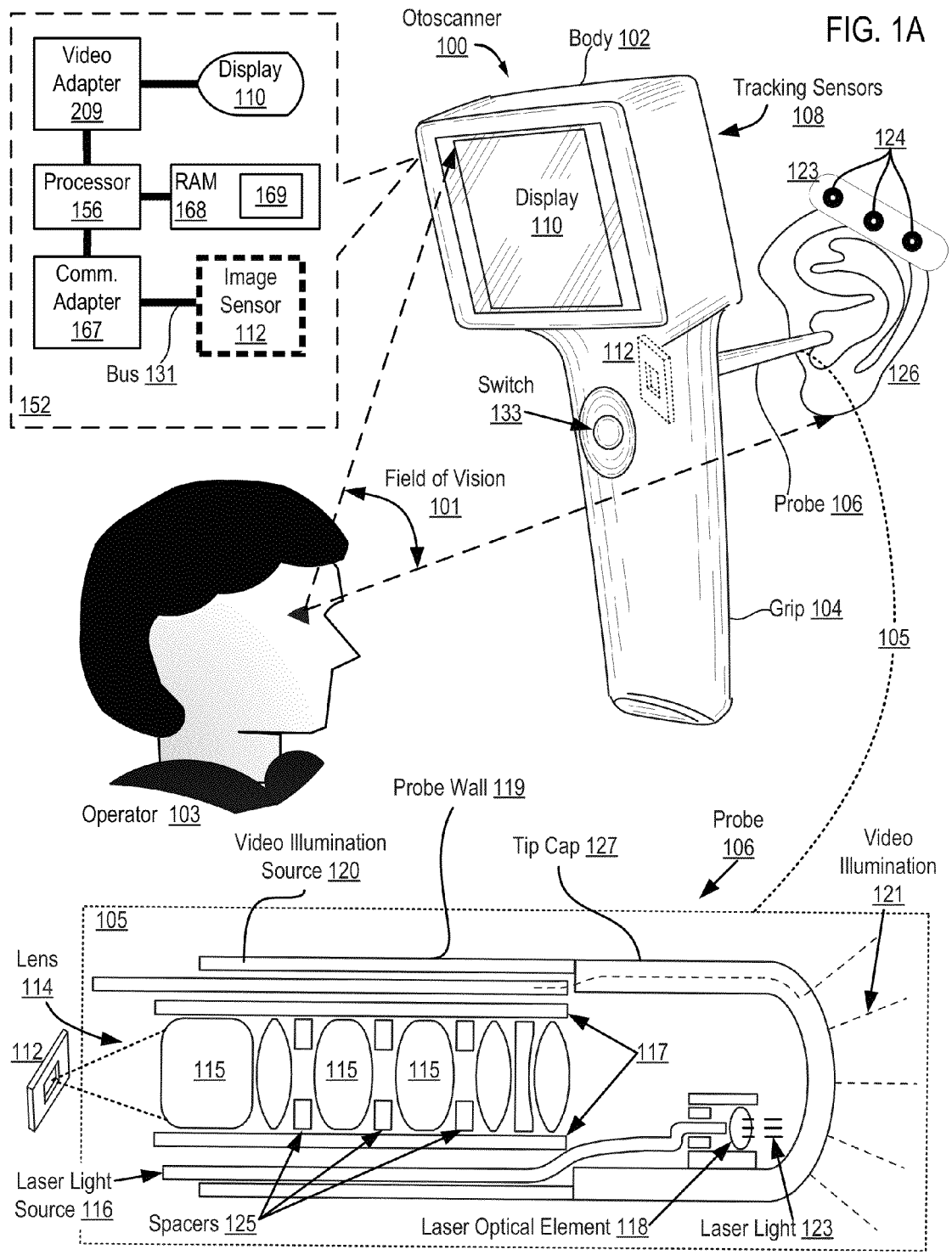
FIG. 1A sets forth a line drawing of an example otoscanner.

Example otoscanning apparatus and methods according to embodiments of the present invention are described with reference to the accompanying drawings, beginning with FIG. 1A. FIG. 1A sets forth a line drawing of an example otoscanner (100) having an otoscanner body (102). The otoscanner body (102) includes a hand grip (104). The otoscanner body (102) has mounted upon it an ear probe (106), a tracking illumination emitter (129 on FIG. 2), a plurality of tracking illumination sensors (108, not visible on FIG. 1A, visible on FIG. 2), and a display screen (110). The otoscanner body has mounted within it an image sensor (112).

The display screen (110 is coupled for data communications to the image sensor (112, and the display screen (110 displays images of the scanned ear (126). FIG. 1A includes a callout (152) that schematically illustrates an example of the display screen (110) coupled for data communications to the image sensor (112) through a data communications bus (131), a communications adapter (167), a data processor (156), and a video adapter (209). The displayed images can include video images of the ear captured by the image sensor (112) as the probe is moved within a scanned ear (126). The displayed images can include real-time constructions of 3D images of the scanned ear, such as the one illustrated on FIG. 13. The displayed images can also include snapshot images of portions of the scanned ear.

The display screen (110) is positioned on the otoscanner body (102) in relation to the ear probe (106) so that when the ear probe (106) is positioned for scanning, both the display screen (110) and the ear probe (106) are visible to any operator (103) of the otoscanner (100). In the example of FIG. 1A, the display screen (110) positioned on the otoscanner body (102) in relation to the ear probe (106) so that when the ear probe (106) is positioned for scanning, both the display screen (110) and the ear probe (106) are visible to a operator operating the otoscanner (100) is implemented with the ear probe (106) mounted on the scanner body (102) between the hand grip (104) and the display screen (110) and the display screen (110) mounted on the opposite side of the scanner body (102) from the ear probe (106) and distally from the hand grip (104). In this way, when an operator takes the grip in the operator's hand and position the probe to scan an ear, both the probe and the display are easily visible at all times to the operator.

In the example of FIG. 1A, the display screen (110) is positioned on the otoscanner body (102) in relation to the ear probe (106) so that when the ear probe (106) is positioned for scanning, both the display screen (110) and the ear probe (106) are visible to any operator (103) of the otoscanner (100). This is for explanation, and not for limitation. In fact, in some embodiments, the display screen (110) is not positioned on the otoscanner body (102) in any particular relation to the ear probe (106). That is, in some such embodiments, during scanning the ear probe is not visible to the operator or the display screen is not visible to the operator. The ear probe may therefore be located anywhere on the otoscanner body with respect to the display screen if both are integrated into the otoscanner. And furthermore, in some embodiments, the otoscanner may not even have an integrated display screen.

FIG. 1A includes a callout (105) that illustrates the ear probe (106) in more detail. The ear probe (106) includes a wide-angle lens (114) that is optically coupled to the image sensor (112), with the lens and the sensor oriented so as to capture images of surfaces illuminated by light from laser and non-laser light sources in the probe. In the example otoscanner probe (106) of FIG. 1A, the wide angle lens (114) has a sufficient depth of field so that the entire portion of the surface of an ear (126) illuminated by laser light is in focus at the image sensor (112). An image of a portion of the scanned ear is said to be in focus if light from object points on the surface of the ear is converged as much as reasonably possible at the image sensor (112), and out of focus if light is not well converged. The term "wide angle lens" as used herein refers to any lens configured for a relatively wide field of view that will work in tortuous openings such as an auditory canal. For example, for an auditory canal, a 63 degree angle results in a lens-focal surface offset about equal to the maximum diameter of the auditory canal that can be scanned with a centered ear probe. The focal surface of a 60 degree lens (a fairly standard sized wide angle lens) is equal to the diameter, resulting in a forward focal surface of about 6 mm, which typically is short enough to survive the second bend in an auditory canal which is at about a 6 mm diameter. For scanning auditory canals, therefore, wide angle lenses typically are 60 degrees or greater. Other functional increments include 90 degrees with its 2:1 ratio allowing a forward focal surface distance of about 3 mm, allowing an ear probe to be fairly short. Lenses that are greater than 90 degrees are possible as are lenses that include complex optical elements with sideways only views and no forward field of view. According to some embodiments, laser light is emitted from the otoscanner probe in the form of a ring or in the form of a fan, and the wide angle lens provides the same sufficient depth of field to portions of a scanned ear as illuminated by all such forms of laser.

The wide angle lens (114) can view relatively proximate lateral portions of a surface with high precision due to overlap of its focal surface with a pattern of projected laser light. The term "focal surface" refers to a thickness within a range of focus of the wide angle lens that is capable of achieving a certain base line resolution, such as being able to discern a 50 micrometer feature or smaller. In an embodiment, for example, lateral positioning of a pattern of projected laser light within the focal surface can allow one pixel to be equivalent to about 50 micrometers. Such a focal surface itself would have a bell curve distribution of resolution that would allow variations in overlap or thickness of the focal surface and the width of the lateral portion of reflected laser light which, as described in more detail below, has its own curved distribution across its thickness.

Wide angle lenses (114) in embodiments typically have a reasonably low distortion threshold to meet resolution goals. Most wide angle lenses can be as high as −80 percent or −60 percent distortion that would need to be compensated by improved accuracy in other areas such as placement of the focal surface and lateral portion of projected patterns of laser light. There is therefore no set threshold although collectively the various components are preferably tuned to allow a 50 micrometer or better resolution for lateral distances from the optical axis of the wide angle lens. A distortion of −40 percent or better provides a workable field of view for scanning auditory canals.

Figure 6:
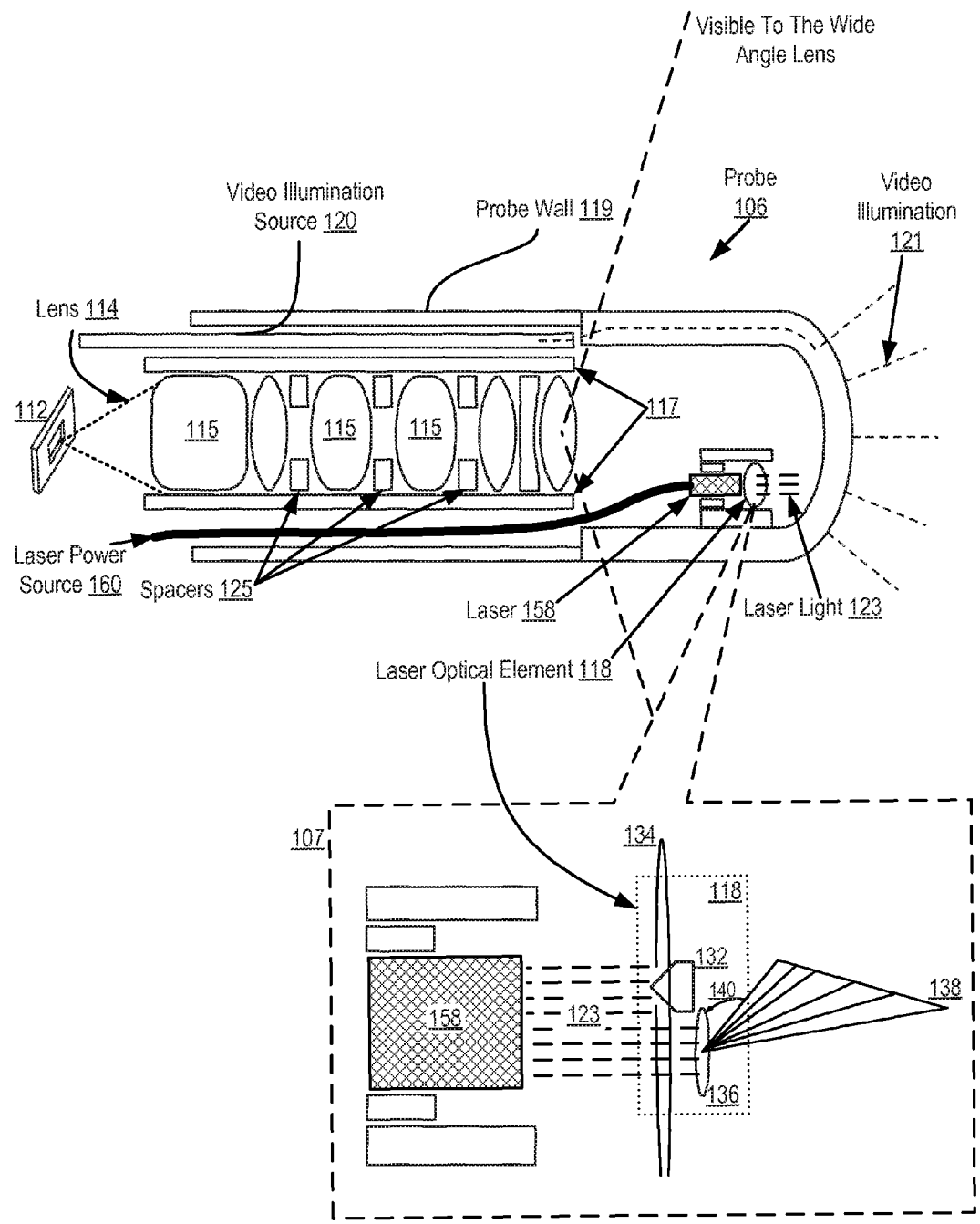
FIG. 6 sets forth a line drawing of an example ear probe (106) of an otoscanner according to embodiments of the present invention.

The ear probe (106) includes a laser light source (116), a laser optical element (118), and a source of non-laser video illumination (120). The laser light source (116) delivers laser light (123) that illuminates surfaces of a scanned ear (126) with laser light, and the video illumination source delivers video illumination that illuminates surfaces of a scanned ear with non-laser light (121). In the example of FIG. 1A, the laser light source (116) in the ear probe is implemented as an optical fiber (130) that conducts laser light to the ear probe (106) from a laser outside the probe (106). In fact, in the example of FIG. 1A, both sources of illumination (116, 120) are implemented with optical fiber that conduct illumination from, for example, sources mounted elsewhere in the otoscanner body, a white light-emitting-diode ('LED') for the non-laser video illumination (121) and a laser diode or the like for the laser light (123). For further explanation, an alternative structure for the laser light source is illustrated in FIG. 6, where the laser light source is implemented as an actual laser (158), such as, for example, an on-chip laser diode, mounted directly on mounting structures disposed in the probe itself. In the example of FIG. 6, a laser power source (160), electrical wiring, replaces the optical fiber (116 on FIG. 1A) in the overall structure of the probe, connecting a power supply outside the probe to the laser (158). In the examples both of FIG. 1A and FIG. 6, the laser light (123) is collimated by a laser optical element (118), and the non-laser video illumination (121) is diffused by a transparent top cap (127) mounted on the tip of the probe. Laser illumination from the laser light source (116) can be on continuously with the LED pulsed or both the laser and the LED can be pulsed, for example.

The otoscanner (100) in the example of FIG. 1A provides a mode switch (133) for manual mode switching between laser-only mode, in which a laser-illuminated scan of an ear is performed without video, and a video-only mode in which non-laser light is used to illuminate a scanned ear and normal video of the ear is provided on the display screen (110). The laser light is too bright to leave on while capturing video images, however, so with manual switching, only one mode can be employed at a time. In some embodiments of the kind of otoscanner illustrated for example in FIG. 1A, therefore, the image sensor is configured so as to capture images at a video frame rate that is twice a standard video frame rate. The frame rate is the frequency at which an imaging sensor produces unique consecutive images called frames. Frame rate is typically expressed in frames per second. Examples of standard video frame rates include 25 frames per second as used in the Phase Alternating Line or 'PAL' video standard and 30 frames per second as used in the National Television System Committee or 'NTSC' video standard. At twice a standard frame rate, video and laser-illuminated images can be captured on alternate frames while leaving the frame rate for each set to a standard video rate. In such embodiments, the non-laser video illumination (120, 121) is left on at all times, but the laser light source (116) is strobed during capture by the image sensor of alternate video frames. Video frames are captured by the image sensor (112) when only the non-laser video illumination illuminates the scanned ear, that is, on the alternate frames when the laser light source (116) is strobed off. Then laser-illuminated images for constructing 3D images are captured by the image sensor (112) only when strobed laser light illuminates the scanned ear, that is, during the alternate frames when the laser light source (116) is strobed on, overwhelming the always-on non-laser video illumination.

Figure 1B:
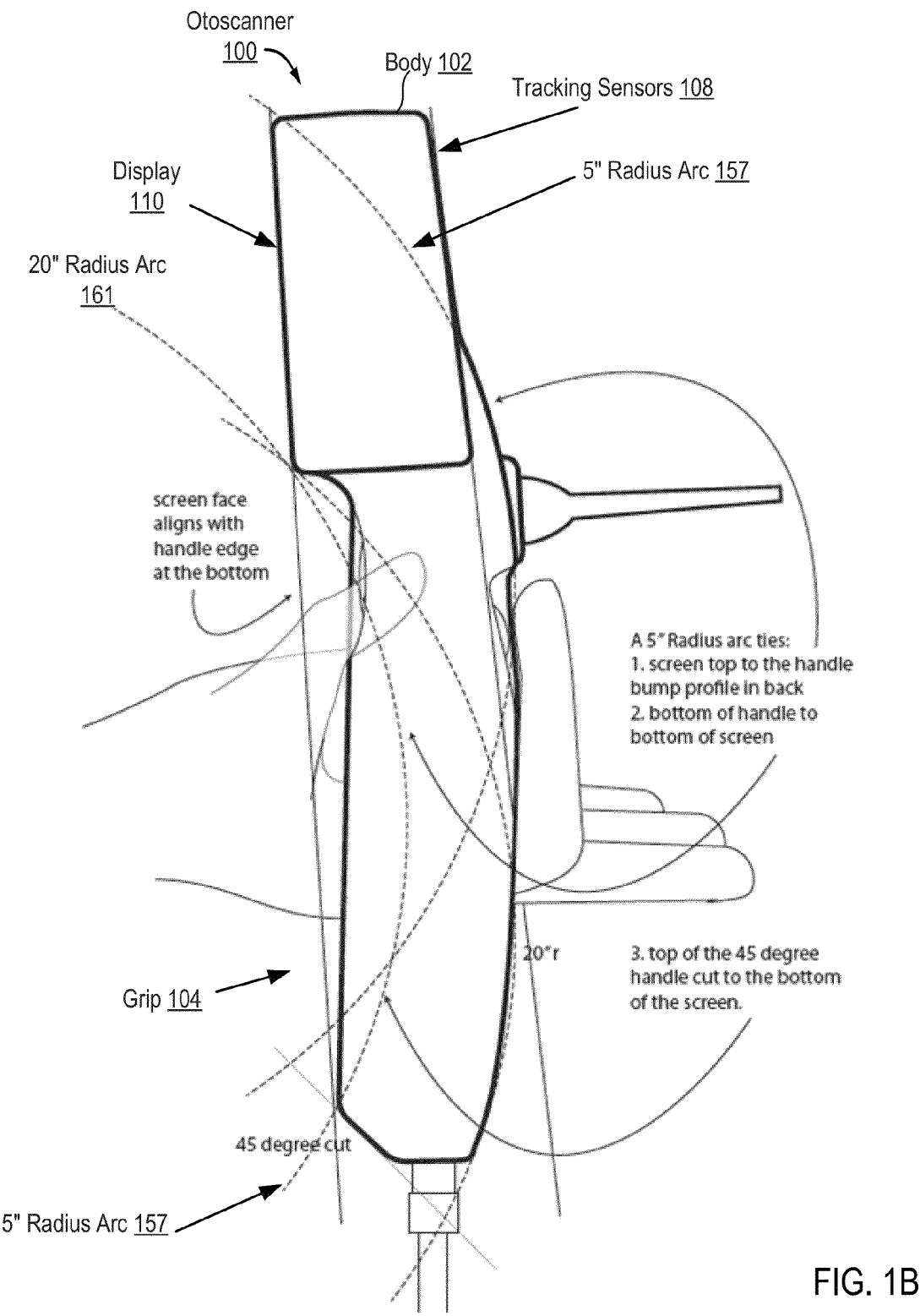
FIGS. 1B-1E set forth line drawings of further example otoscanners.

For further explanation, FIGS. 1B-1E set forth line drawings of further example otoscanners, illustrating additional details of example embodiments. In the example of FIG. 1B, an otoscanner (100) includes a body (102), display (110), tracking sensors (108), and grip (104), all implemented in a fashion similar to that of the otoscanner describes and illustrated above with reference to FIG. 1A. The example of FIG. 1B includes 5-inch radius arcs (157) that defines and connect the screen top to a grip bump profile on the back of the otoscanner body, the bottom of the grip to the bottom of the display screen, and the top of a 45-degree cut at the bottom of the grip to the bottom of the display screen. In addition, the example of FIG. 1B includes a 20-inch radius arc (161) that defines the overall curvature of the grip (104).

Figure 1C:
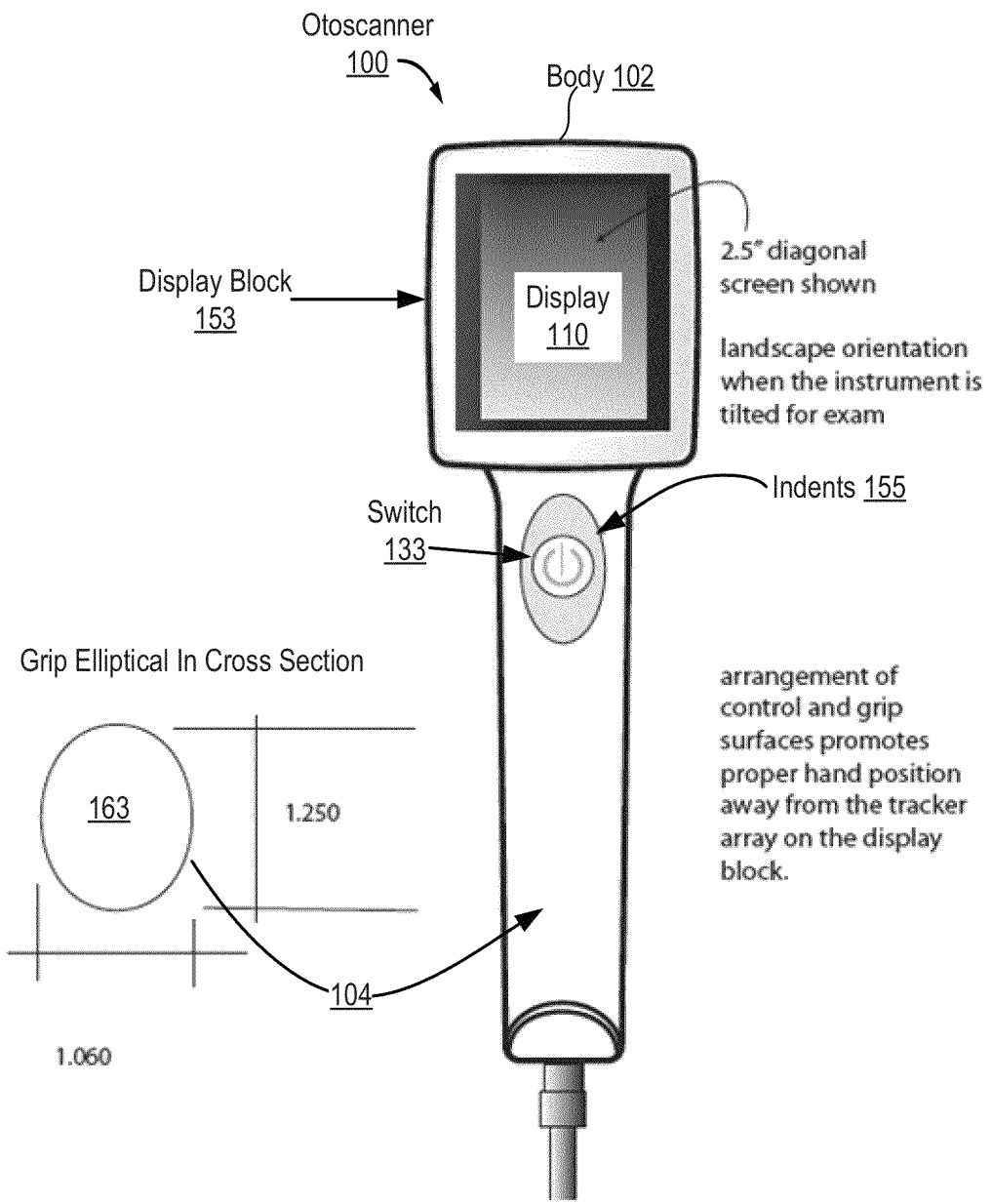

In the example of FIG. 1C, an otoscanner (100) includes a body (102), display (110), tracking sensors (108), and grip (104), all implemented in a fashion similar to that of the otoscanner describes and illustrated above with reference to FIG. 1A. The example of FIG. 1C includes a description of the grip (104) as elliptical in cross section, conforming to an ellipse (163) in this example with a major axis 1.25 inches in length and a minor axis of 1.06 inches. The example of FIG. 1C also includes a display screen 2.5 to 3.5 inches, for example, in diagonal measure and capable of displaying high-definition video. The display screen (110) is also configured with the capability of displaying images in portrait orientation until the otoscanner body is oriented for scanning an ear, at which time the display can change to a landscape orientation. Indents (155) are provided around control switches (133) both on front and back of the grip (104) that guide operator fingers to the control switches with no need for an operator takes eyes off the display screen or the probe to look for the switches.

Figure 1D:
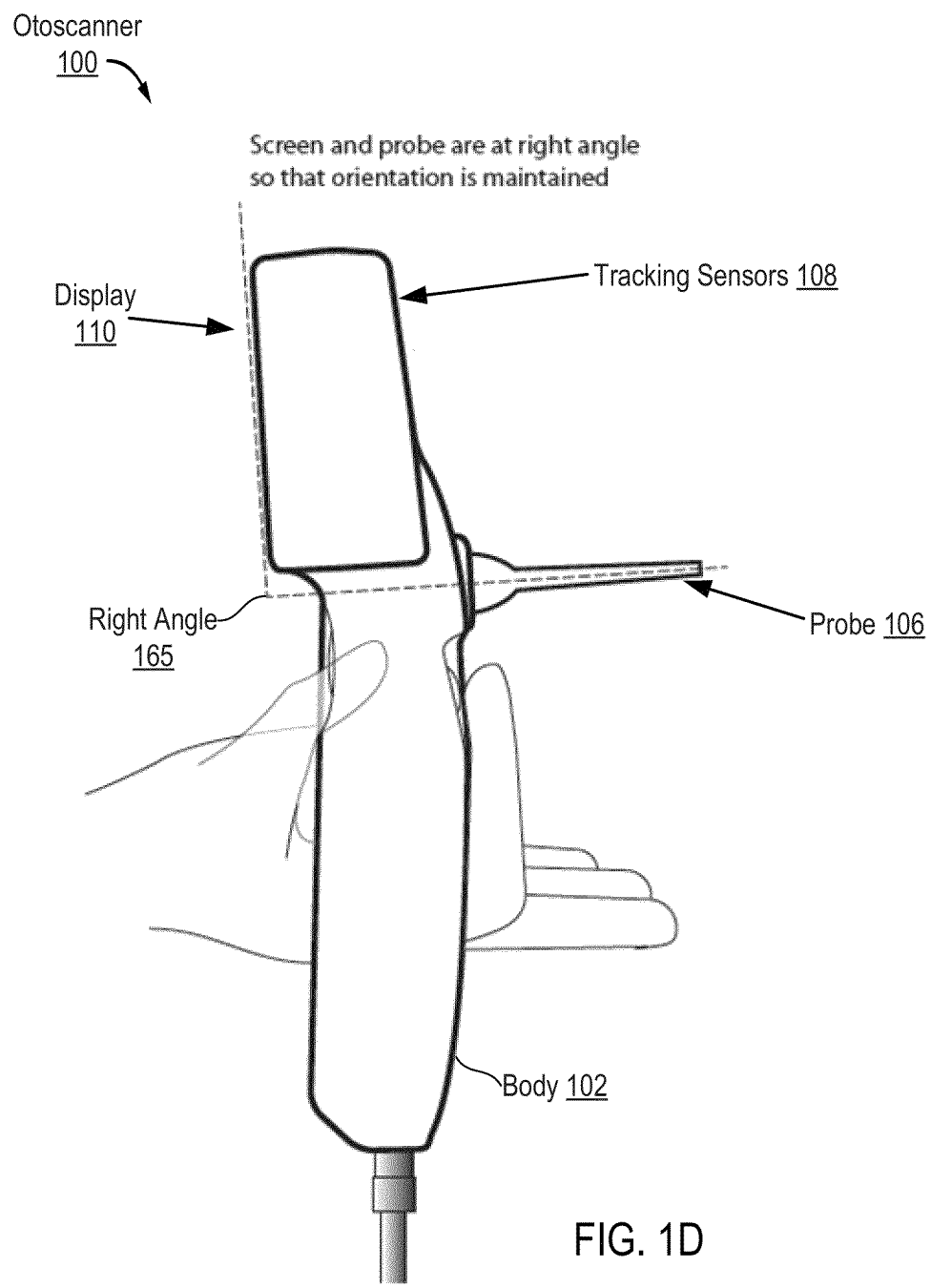

In the example of FIG. 1D, an otoscanner (100) includes a body (102), display (110), tracking sensors (108), and grip (104), all implemented in a fashion similar to that of the otoscanner describes and illustrated above with reference to FIG. 1A. The example of FIG. 1D includes an illustration of the display screen (110) oriented at a right angle (165) to a central axis of the ear probe (106) so as to maintain the overall orientation of the display as it will be viewed by an operator.

Figure 1E:
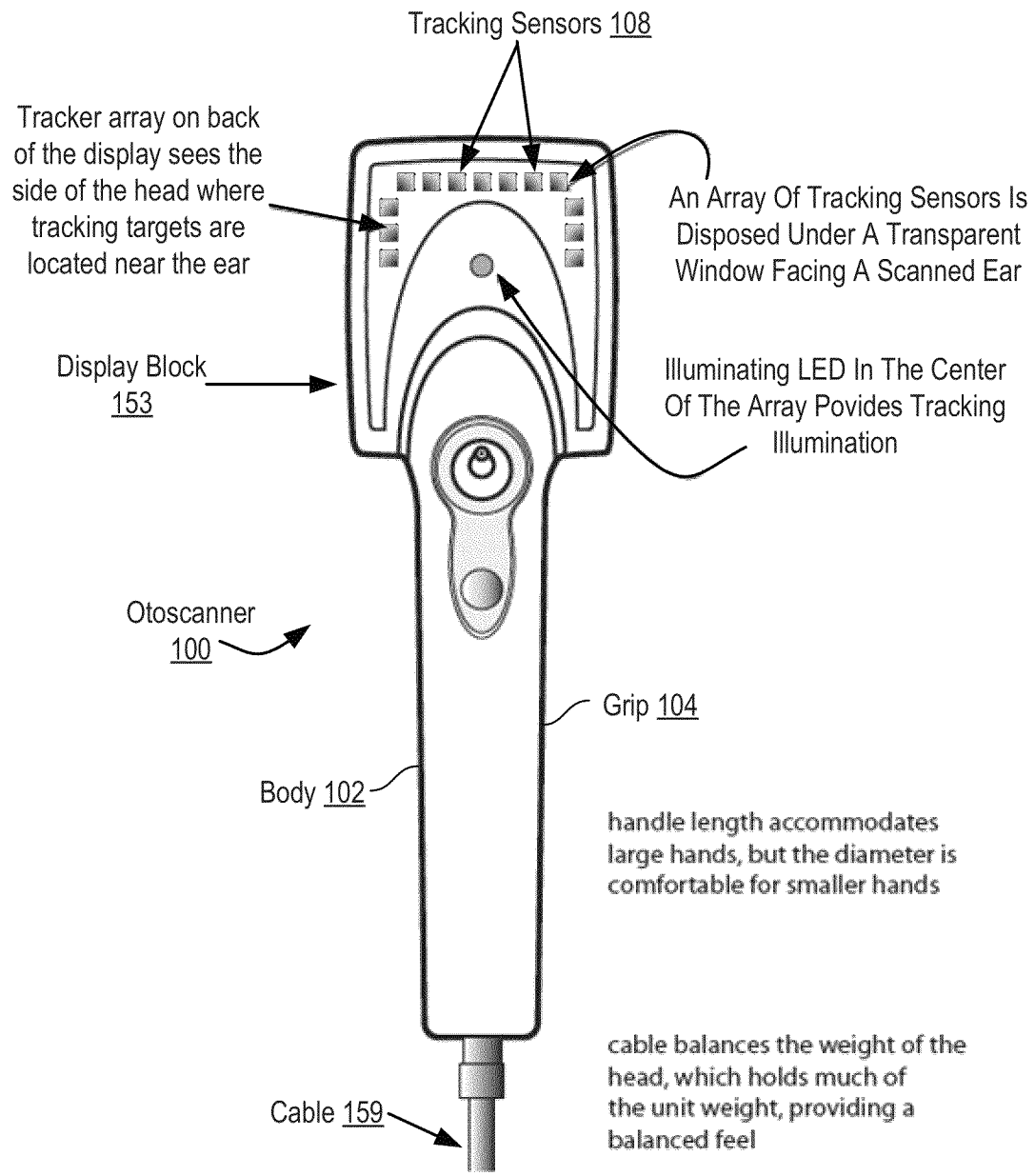

In the example of FIG. 1E, an otoscanner (100) includes a body (102), tracking sensors (108), and grip (104), all implemented in a fashion similar to that of the otoscanner describes and illustrated above with reference to FIG. 1A. The example of FIG. 1E includes an illustration of the orientation of an array of tracking sensors (108) on the back of the display, that is, on the opposite side of the otoscanner body from the display screen, oriented so that the tracking sensor can sense reflections of tracking illumination from tracking targets fixed in position with respect to a scanned ear. The tracking sensor are disposed behind a window that is transparent to the tracking illumination, although it may render the tracking sensors themselves invisible in normal light, that is, not visible to a person. The example of FIG. 1E also includes a grip (104) whose length accommodates large hands, although the diameter of the grip is still comfortable for smaller hands. The example of FIG. 1E also includes a cable (159) that connects electronic components in the otoscanner body (102) to components outside the body. The cable (159) balances the weight of the display block, which holds much of the weight of the otoscanner body. The use of the cable (159) as shown in FIG. 1E provides to an operator an overall balanced feel of the otoscanner body.

Figure 2:
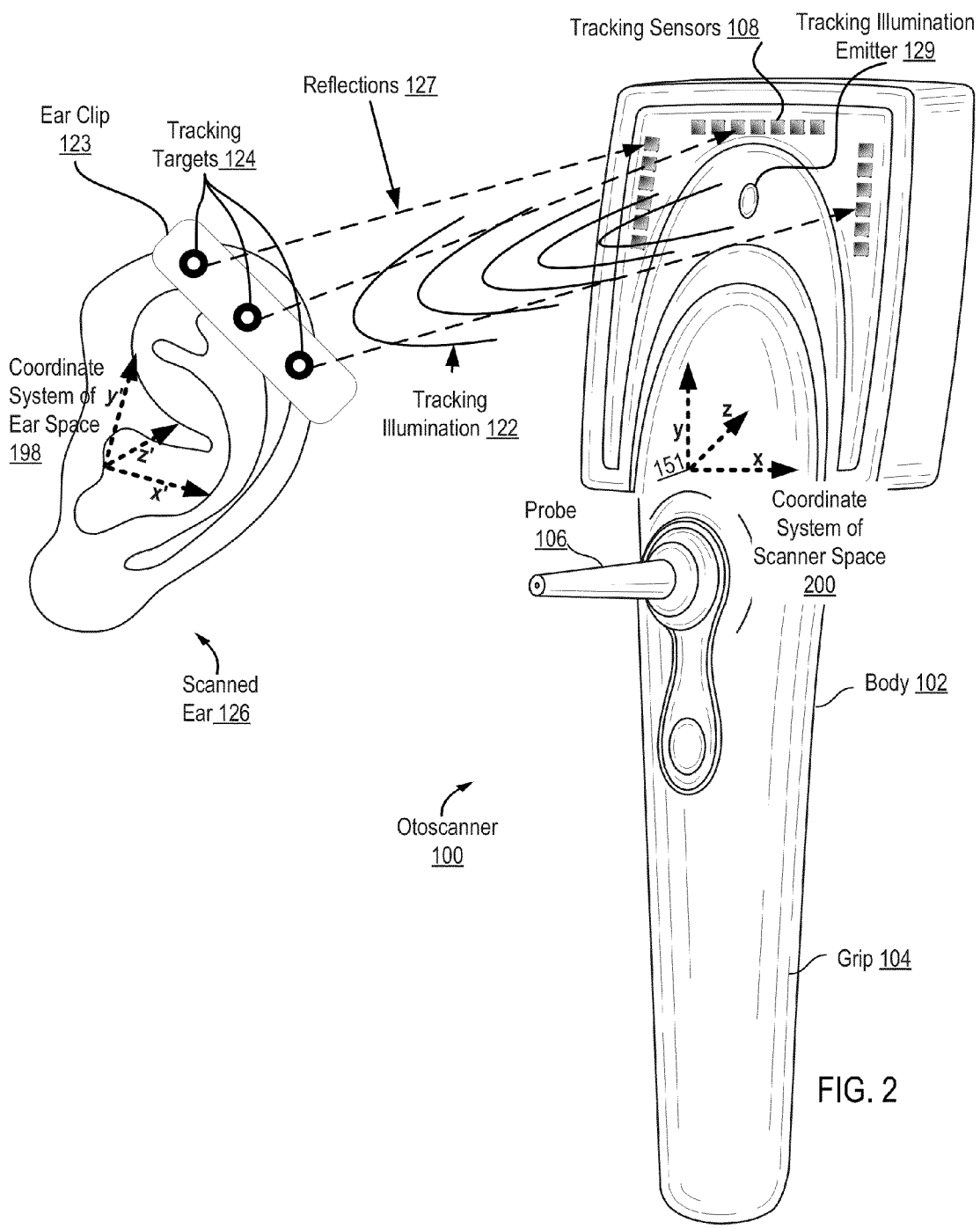
FIG. 2 sets forth a line drawing of an even further example otoscanner.
Figure 13:
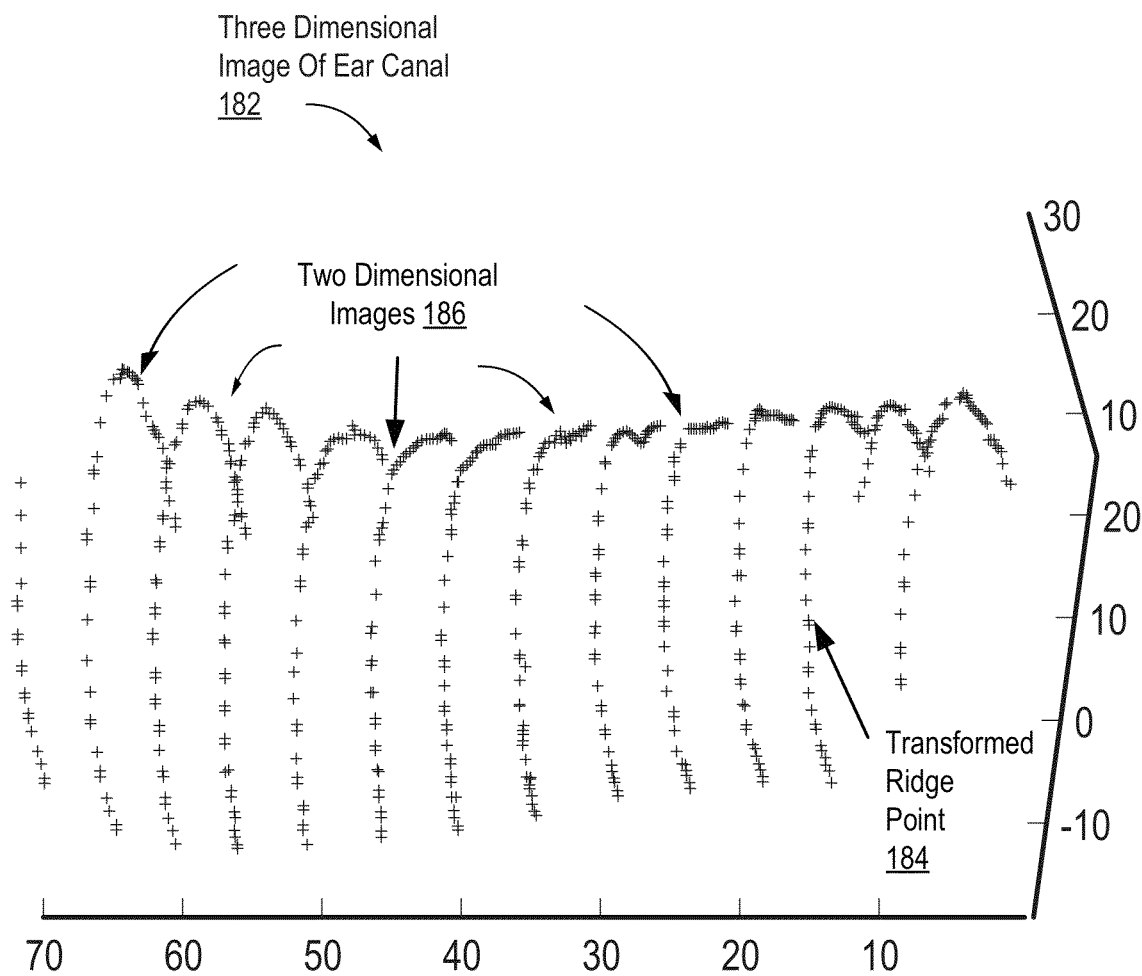
FIG. 13 sets forth a line drawing illustrating an example three-dimensional image of an ear canal constructed by use of a data processor from a sequence of 2D images.

Referring again to FIG. 1A, the image sensor (112) is also coupled for data communications to a data processor (128), and the data processor (128) is configured so that it functions by constructing, in dependence upon a sequence of images captured when the scanned ear is illuminated by laser light and tracked positions of the ear probe inferred from reflections of tracking illumination sensed by the tracking illumination sensors, a 3D image of the interior of the scanned ear, such as, for example the image illustrated in FIG. 13. For further explanation, FIG. 2 sets forth a line drawing of an example otoscanner with a number of tracking illumination sensors (108) disposed upon the otoscanner body (102) so as to sense reflections (127) of tracking illumination (122) emitted from the tracking illumination emitter (129) and reflected from tracking targets (124) installed at positions that are fixed relative to the scanned ear (126). The tracking illumination sensors (127) are photocells or the like disposed upon or within the opposite side of the display block from the display and organized so as to distinguish angles and brightness of tracking illumination reflected from tracking targets. In the example of FIG. 2, the tracking targets (124) are implemented as retroreflectors, and the tracking illumination (122) is provided from a tracking illumination source or emitter (129), such as an LED or the like, mounted on the otoscanner body (102). In at least some embodiments, the tracking illumination (122) is infrared.

In the example of FIG. 2, the tracking sensors (108) are mounted directly on or within the otoscanner (100). In other embodiments, the tracking sensors are mounted elsewhere, in other locations fixed within scanner space, not on or within the otoscanner itself. In such embodiments, a stand alone or separate tracking system can be used. Such embodiments can include one or many tracking sensors, one or many light sources. Some embodiments exclude tracking entirely, instead relying of the stability of an object to be scanned. To the extent that such an object is an ear, then the person to whom the ear belongs must sit very still during the scan. Other embodiments use a tripod for mounting the tracking systems of tracking illumination sensors.

The data processor (128) configured so that it constructs a 3D image of the interior of the scanned ear can be implemented, for example, by a construction module (169) of computer program instructions installed in random access memory ('RAM') (168) operatively coupled to the processor through a data communications bus. The computer program instructions, when executed by the processor, cause the processor to function so as to construct 3D images based on tracking information for the otoscope body or probe and corresponding images captured by the image sensor when a surface of a scanned ear is illuminated with laser light.

Figure 3A:
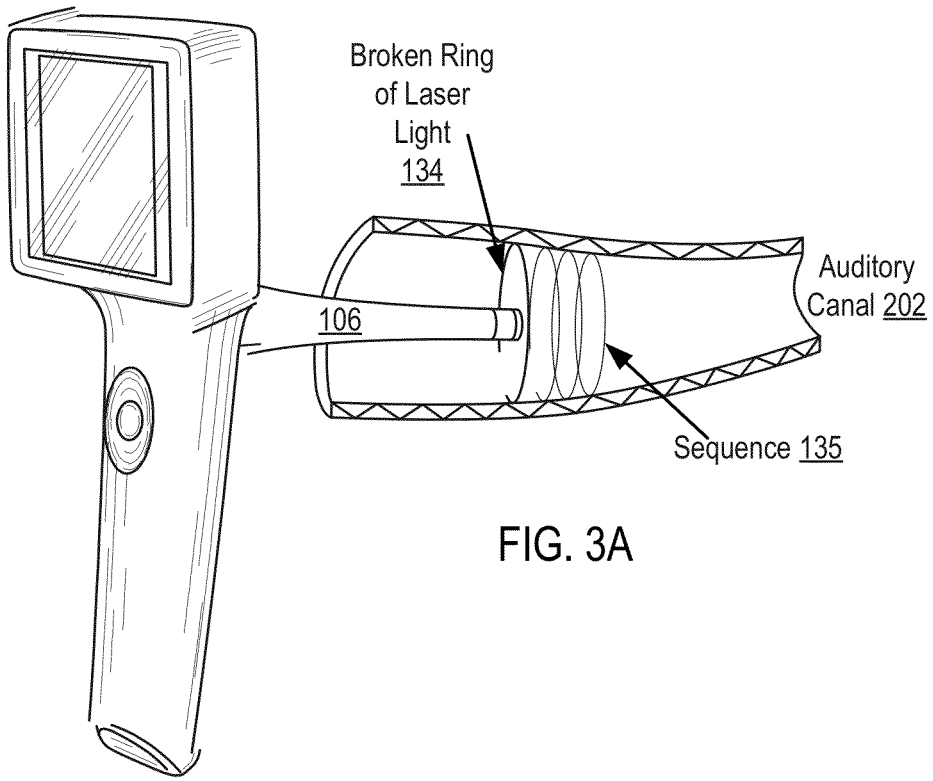
FIGS. 3A and 3B illustrate projections of laser light onto surfaces of a scanned ear.

For explanation of a surface of a scanned ear illuminated with laser light, FIG. 3A sets forth a line drawing of a projection onto a surface of an auditory canal of a ring of laser, the ring projected from a conical reflector (132 on FIG. 8A) into a plane which forms a broken ring (134) as the plane of laser light encounters the inner surface of the auditory canal. As the ear probe (106) moves through the auditory canal (202), an image sensor in the otoscanner captures a sequence (135) of images of the interior of the auditory canal illuminated by rings of projected laser light. Each such image is associated with tracking information gathered by tracking apparatus as illustrated and described with regard to FIG. 2. A combination of such images and associated tracking information is used according to embodiments of the present invention to construct 3D images of a scanned ear.

Figure 3B:
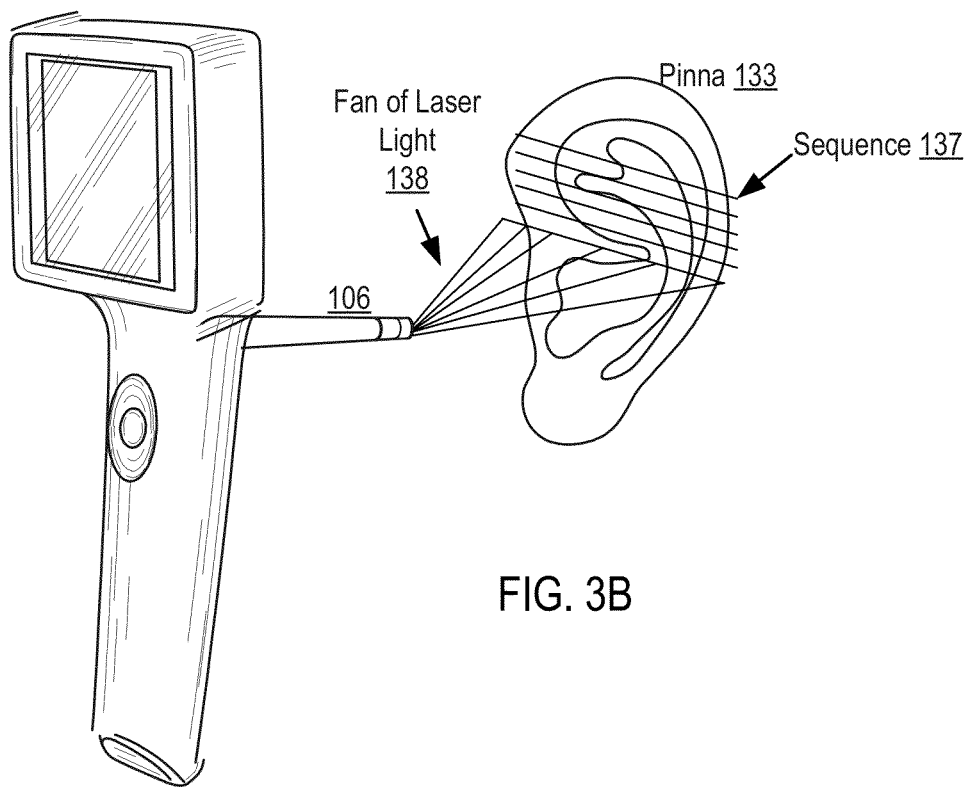

For further explanation of a surface of a scanned ear illuminated with laser light, FIG. 3B sets forth a line drawing of a projection onto surface of a pinna or aurical of a scanned ear of a fan (138) of laser, the fan projected from a diffractive laser lens (136 on FIG. 7A) into a fan shape which illuminates the surface of the pinna, conforming to the surface of the pinna as the fan of laser light encounters the pinna. As an ear probe (106) is moved to scan the pinna, an image sensor in the otoscanner captures a sequence (137) of images of the surface of the pinna as illuminated by the fan (138) of projected laser light. Each such image is associated with tracking information gathered by tracking apparatus as illustrated and described with regard to FIG. 2. A combination of such images and associated tracking information is used according to embodiments of the present invention to construct 3D images of a scanned ear.

Figure 4:
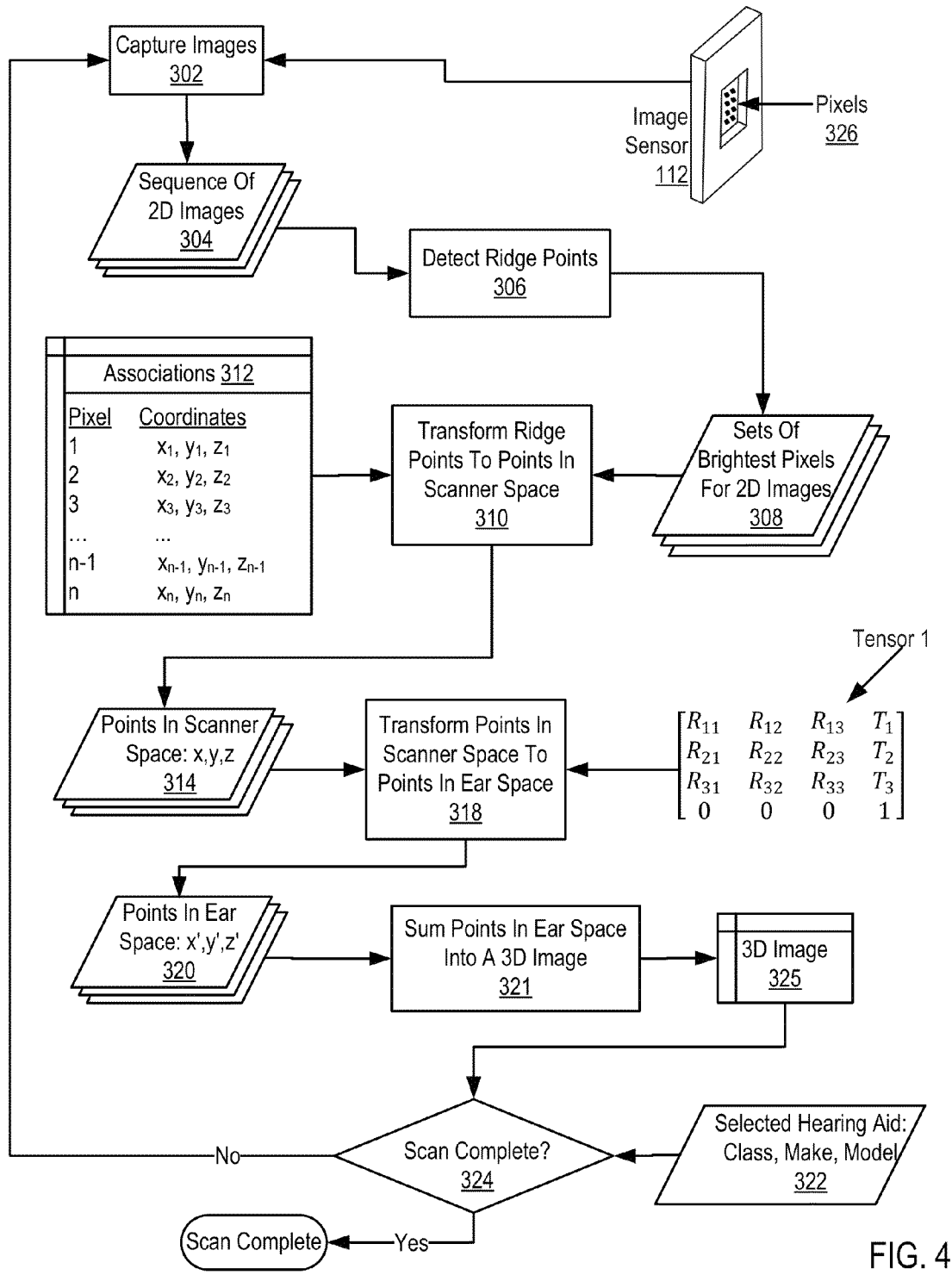
FIG. 4 sets forth a flow chart illustrating an example method of constructing a 3D image of a scanned ear.

For further explanation of construction of 3D images with an otoscanner according to embodiments of the present invention, FIG. 4 sets forth a flow chart illustrating an example method of constructing a 3D image of a scanned ear. The method of FIG. 4 includes capturing (302), with an image sensor (112) of an otoscanner of the kind described above, a sequence (304) of 3D images of surfaces of a scanned ear. The sequence of images is a sequence of 2D images of surfaces of the scanned ear illuminated with laser light as described above. The image sensor includes an array of light-sensitive pixels, and each image (304) is a set of pixel identifiers such as pixel numbers or pixel coordinates with a brightness value for each pixel. The sequence of 2D images is used as described to construct a 3D image.

Figure 10:
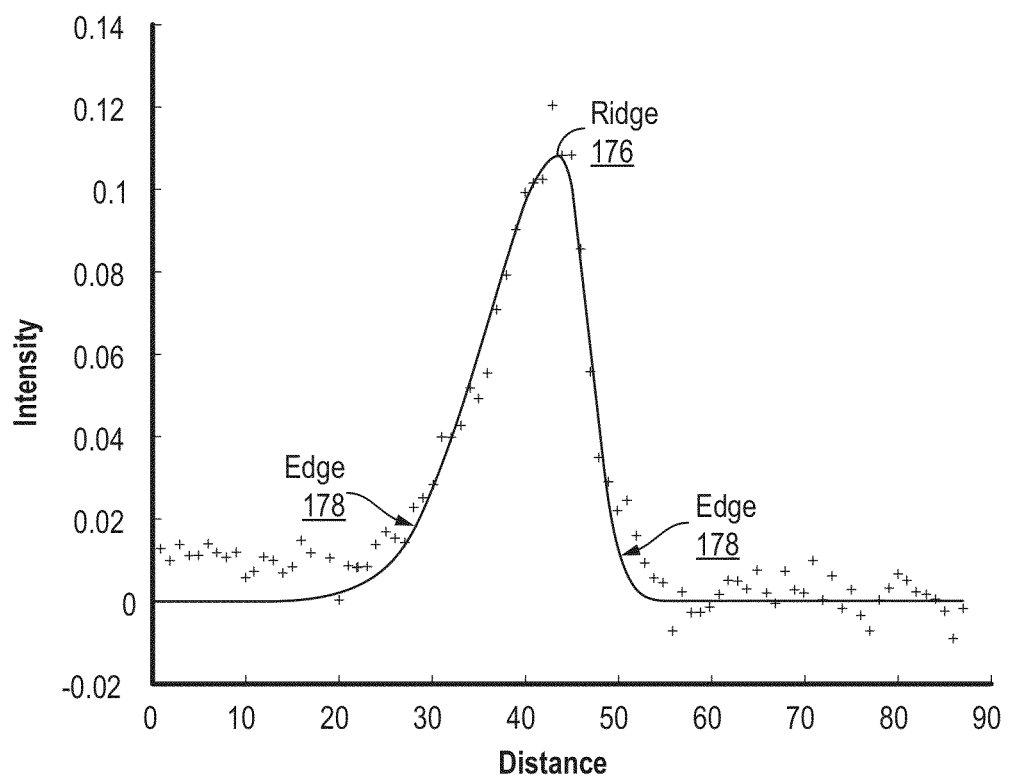
FIG. 10 illustrates reflected laser light intensity varying in a bell-curve shape with a thickness of a section of projected laser light.

The method of FIG. 4 also includes detecting (306) ridge points (308) for each 2D image. Ridge points for a 2D image make up a set of brightest pixels for the 2D image, a set that is assembled by scanning the pixel brightness values for each 2D image and selecting as ridge points only the brightest pixels. An example of a 2D image is set forth in FIG. 10, illustrating a set of brightest pixels or ridge points (176) that in turn depicts a c-shaped broken ring of laser light reflecting from a surface of an auditory canal of a scanned ear.

The method of FIG. 4 also includes transforming (318) the ridge points to points in scanner space. The transforming (318) in this example is carried out by use of a table of predefined associations (312) between each pixel in the image sensor (112) and corresponding points in scanner space. Each record of table (312) represents an association between a pixel (326) of the image sensor (112) and a point in scanner space (200 on FIG. 2). In the example of table (312), n pixels are identified with numbers, 1, 2, 3, . . . , n−1, n. The pixels of the image sensor can be identified by their x,y coordinates in the image sensor itself, or in other ways as will occur to those of skill in the art. The correspondence between pixels and points in scanner space can be established as described and illustrated below with reference to FIG. 12, triangulation according to equations 2-8. Such triangulation can be carried out by data processor and algorithm for each pixel of each captured frame from the image sensor, although that is computationally burdensome, it is feasible with a fast processor. As a less computationally intense alternative, the triangulation can be carried out once during manufacture or calibration of an otoscanner according to embodiments of the present invention, with the results stored, for example, in a structure similar to Association table (312). Using such stored associations between pixels and points in scanner space, the process of transforming (310) ridge points to points in scanner space is carried out with table lookups and the like rather than real time triangulations.

The example table (312) includes two columns, one labeled 'Pixel' that includes values identifying pixels, and another labeled 'Coordinates' that identifies the locations in scanner space that correspond to each pixel. Readers will recognize that in embodiments in which the records in table (312) are sorted as here according to pixel location, then the 'Pixel' column actually would not be needed because the position of coordinates in the 'Coordinates' columns would automatically index and identify corresponding pixels. In embodiments that omit the 'Pixel' columns based on such reasoning, the Associations table (312) is effectively simplified to an array of coordinates. In fact, the data structures of table and array are not limitation of the present invention, but instead are only examples of data structures by which can be represented correspondence between pixels and points in scanner space. Readers will recognize that many data structures can be so used, including, for example, C-style structures, multi-dimensional arrays, linked lists, and so on.

The method of FIG. 4 also includes transforming (318) the points (314) in scanner space (200 on FIG. 2) to points (320) in ear space (198 on FIG. 2). This transforming (318) is carried out according to a relationship between an origin (151 on FIG. 2) of a coordinate system defining scanner space (200 on FIG. 2) and an origin (150 on FIG. 2) of another coordinate system defining ear space (198 on FIG. 2). That is, scanner space is both translated and rotated with respect to ear space, and this relationship differs from frame to frame as an otoscanner is moved in ear space during a scan. The relationship for each frame is expressed as Tensor 1.

$$\begin{bmatrix} R_{11} & R_{12} & R_{13} & T_1 \\ R_{21} & R_{22} & R_{23} & T_2 \\ R_{31} & R_{32} & R_{33} & T_3 \\ 0 & 0 & 0 & 1 \end{bmatrix} \quad \text{Tensor 1}$$

The T values in Tensor 1 express the translation of scanner space with respect to ear space, and the R value express the rotation of scanner space with respect to ear space. With these values in Tensor 1, the transformation of points in scanner space to points in ear space is carried out according to Equation 1.

$$\begin{bmatrix} x' \\ y' \\ z' \\ 1 \end{bmatrix} \equiv \begin{bmatrix} R_{11} & R_{12} & R_{13} & T_1 \\ R_{21} & R_{22} & R_{23} & T_2 \\ R_{31} & R_{32} & R_{33} & T_3 \\ 0 & 0 & 0 & 1 \end{bmatrix} \begin{bmatrix} x \\ y \\ z \\ 1 \end{bmatrix} \quad \text{Equation 1}$$

Equation 1 transforms by matrix multiplication with Tensor 1 a vector representing point x,y,z in scanner space into a vector representing point x',y',z' in ear space. The transforming (318) of points in scanner space to points in ear space can be carried out by establishing Tensor 1 for each image scanned from the image sensor and applying Equation 1 to each point (314) in scanner space represented by each pixel in each image.

The method of FIG. 4 also includes summing (321) the points in ear space into a 3D image (325) of an ear. The results of such summing are shown schematically in FIG. 13, and an actual 3D image of a scanned ear is set forth in FIG. 14. The image in FIG. 14 was created using the transformed points in ear space as such to display a 3D image. Such a set of points is a mathematical construct. In 3D computer graphics generally, 3D modeling is developing a mathematical representation of a three-dimensional surface of an object (living or inanimate). The products of such processes are called 3D images or 3D models. Such images can be displayed as a two-dimensional image through a process called 3D rendering or used in a computer simulation of physical phenomena. Such an image or model can also be used to create an actual three-dimensional object of a scanned object, such as a scanned ear, using a 3D model as an input to a CAD/CAM process or a 3D printing device.

The method of FIG. 4 also includes determining (324) whether a scan is complete. This determination is carried out by comparing the summed set of points in ear space that now make up a 3D image of the scanned ear for completeness by comparing the 3D image with scanning requirements (322) as specified for a particular, pre-selected class, make, and model of an object to be worn in the ear, an auditory bud, in-ear headphone, hearing aid, or the like. If the scan is incomplete, portions of the 3D image will not meet the scanning requirements as specified for the class, make, and model of the object to be worn in the ear. Often the incomplete portions of the 3D image will appear as holes in the 3D image.

Not all objects worn in the ear require the same portions of the ear to be scanned. scanning requirements (322) as specified for a particular, pre-selected class, make, and model of an object to be worn in the ear. For example, behind-the-ear hearing aids use a mold that requires the concha of the ear to be scanned, in-the-ear hearing aids require more of the auditory canal to be scanned, invisible-in-the-ear hearing aids require even more of the auditory canal to be scanned than the in-the-ear hearing aids. Each of these different classes of hearing aids (behind-the-ear, in-the-ear, and invisible-in-the-ear) may be used to determine whether a scan is complete by also determining which portions of the ear are to be scanned for the particular class of the hearing aid. Within each class of hearing aid or other object to be worn in the ear the make and model may also affect which portions of the ear are to be scanned to make up a complete scan of the ear. Each of these different makes and models within a class of hearing aids may also be used to determine whether a scan is complete including determining which portions of the ear are to be scanned for the particular class of the hearing aid.

Figure 5:
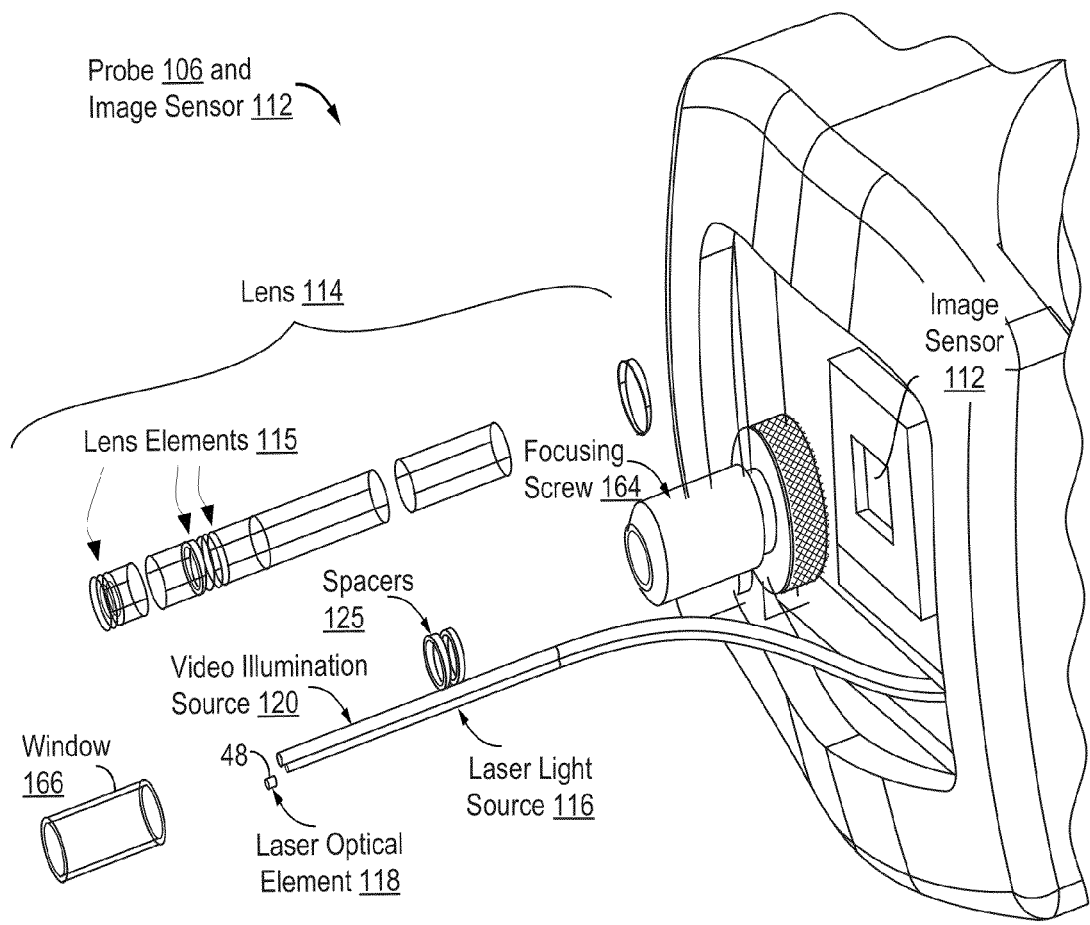
FIG. 5 sets forth a line drawing illustrating additional example features of an ear probe and image sensor of an otoscanner according to embodiments of the present invention.

For further explanation, FIG. 5 sets forth a line drawing illustrating additional example features of an ear probe (106) and image sensor (112) of an otoscanner according to embodiments of the present invention. The probe (106) of FIG. 5 has a wide angle lens (114) that includes a number of lens elements (115) and spacers (125). The wide angle lens (114) of FIG. 5 has a sufficient depth of field so that the entire portion of the interior surface of the ear (126) illuminated by laser light is in focus at the image sensor (112). An image of a portion of the ear is said to be in focus if light from object points on the interior of the ear is converged as much as reasonably possible at the image sensor, and out of focus if light is not well converged. Supporting the wide angle lens 114 of FIG. 5 is a focusing screw 164 that when turned adjusts the focus of the wide angle lens 114 for improved accuracy and for compensating for manufacturing tolerances.

The probe (106) of FIG. 5 also includes a laser light source (116) and a laser optical element (118). In the example of FIG. 5 the laser light source (116) is a fiber optic cable carrying laser light from a laser within the body of the otoscanner to the laser optical element. As mentioned above, in some embodiments of otoscanners according to the present invention, the laser optical element (118) may include a conical laser reflective optical element. In such embodiments, the lens elements (115) of the wide angle lens (114) of FIG. 5 has sufficient depth of field so that the portion of the interior surface of the ear (126) illuminated by laser light is in focus at the image sensor (112) when the interior surface of the ear is illuminated by a ring of laser light created by use of the conical laser reflective optical element and projected through the transparent side walls of the window (166). In some other embodiments of the present invention, the laser optical element (118) may include a diffractive laser optic lens. In such embodiments, the lens elements (115) of the wide angle lens (114) of FIG. 5 has sufficient depth of field so that the portion of the interior surface of the ear (126) illuminated by laser light is in focus at the image sensor (112) when the interior surface of the ear is illuminated by a fan of laser light created by use of a diffractive laser optic lens and projected through the front of the transparent window (116).

In the example of FIG. 5, the image sensor (112) operates at a video frame rate that is twice a standard video frame rate. By operating at twice a standard video frame rage the image sensor may capture usable video of the scanned ear as well as capture images of the scanned ear for constructing 3D images of the scanned ear. In the example of FIG. 5, therefore, the laser light source (116) is strobed during capture by the image sensor (112) of alternate video frames thereby allowing every other video image to be a 2D image for constructing 3D images. The 2D image for constructing 3D images are captured by the image sensor only when the strobed laser light illuminates the scanned ear. Video frames are captured by the image sensor (112) when only the non-laser video illumination from the video illumination source (120) illuminates the scanned ear.

In the example of FIG. 5, the laser light source (116) of FIG. 5 completely overpowers the video illumination source (120). The video illumination source (12) therefore 4 may remain on such that non-laser video illumination is on during operation of the otoscanner. Therefore, when the laser light source (116) is strobed, it completely overpowers the video illumination and each time the laser light source illuminates the scanner ear with laser light images captured by the image sensor are 2D images of the scanned ear for construction of a 3D image.

For further explanation, FIG. 6 sets forth a line drawing of an example ear probe (106) of an otoscanner according to embodiments of the present invention. The ear probe (106) of FIG. 6 is similar to the ear probe of FIG. 1A in that it includes a lens (114) with lens elements (115) and spacers (125), a lens tube (117) a video illumination source, a probe wall (119), and a laser optical element (118). The field of view of the illustrated embodiment, shown by dotted lines, is approximately 150 degrees, although the light pattern (123) may extend laterally out at right angles to the optical axis of the wide angle lens (114). Angles up to 180 degrees are possible but wider angles can be increasingly difficult to minimize distortion. The ear probe (106) of FIG. 6 differs from the ear probe of FIG. 1A in that the laser light source of the ear probe of FIG. 6 is a laser (158) mounted in the probe (106) itself. In the example of FIG. 6 the laser (158) is mounted in the probe and power to the laser is proved by a laser power source (160) delivering power from within the otoscanner body. In some embodiments, the laser may be a mounted on a bare die allowing the laser to be placed directly on a printed circuit board in the ear probe.

Figure 7A:
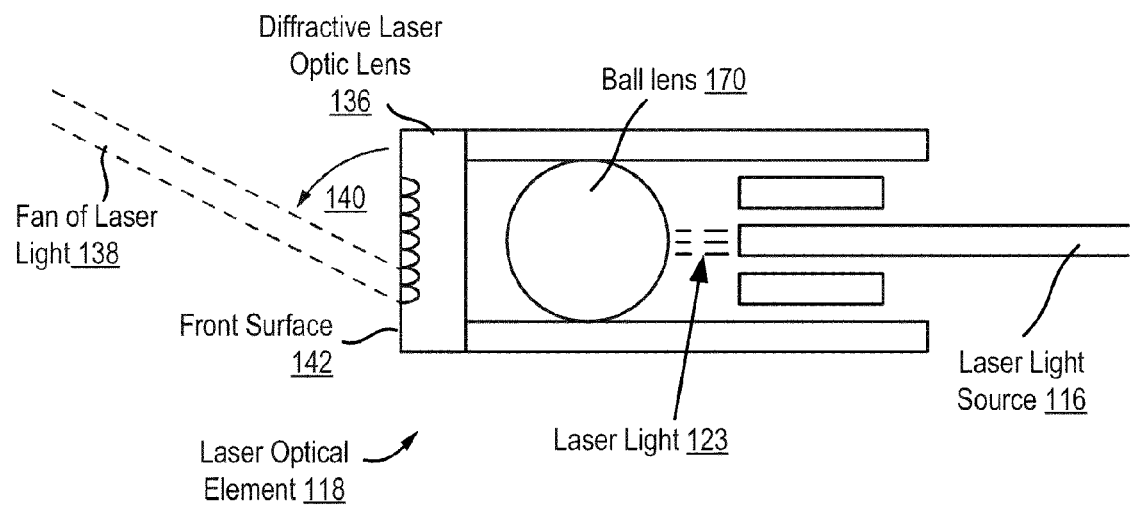
FIGS. 7A and 7B set forth line drawings of an example optical element and a fan of laser light projected from an ear probe having such an optical element.
Figure 7B:
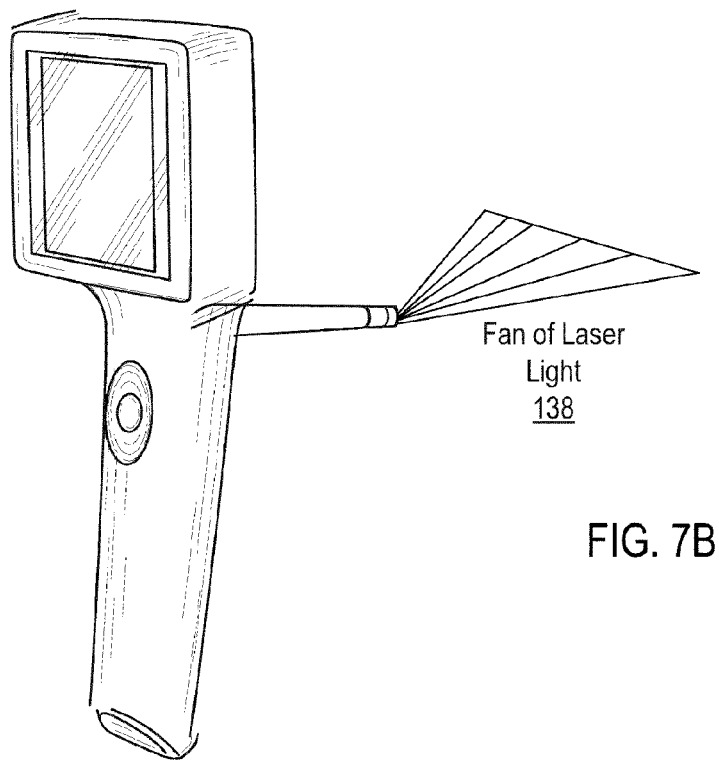

As mentioned above, otoscanners according to embodiments of the present invention may be configured to project a ring of laser light radially from the tip of the distal end of the ear probe, project a fan of laser light forward from the tip of the distal end of the ear probe, or configured to project other shapes of laser light as will occur to those of skill in the art. For further explanation, therefore, FIGS. 7A and 7B set forth line drawings of an optical element (118) useful in scanners according to embodiments of the present invention and a resultant fan of laser light (138) projected from an ear probe having such an optical element. The laser optical element (118) of FIG. 7A comprises a diffractive laser optic lens (136). In the example of FIG. 7A, the laser light source (116) and the diffractive laser optic lens (136) are configured so that when illuminated by the laser light source (116) the diffractive laser optic lens (136) projects upon an interior surface of the ear a fan (138) of laser light at a predetermined angle (140) with respect to a front surface (142) of the diffractive laser optic lens (136). In the example of FIGS. 7A and 7B, laser light from the source of laser light (116) is focused by a ball lens (170) on the diffractive laser optic lens (136). The diffractive laser optic lens (136) diffracts the laser light into a fan (138) of laser light. The diffractive laser optic lens (136) is manufactured to diffract the laser light at a predetermined angle (140) from its front surface (142) into a fan of laser light (138) as illustrated in FIGS. 7A and 7B. In the example of FIG. 7B, the fan of laser light (138) is projected from the distal end of the ear probe of the otoscanner. This is for explanation and not for limitation. In fact, otoscanners according to embodiments of the present invention may be configured to project a fan of laser light from the end of the ear probe closest to the otoscanner body, from positions on the otoscanner body other than the ear probe, or from any other location on the otoscanner as will occur to those of skill in the art.

Figure 8A:
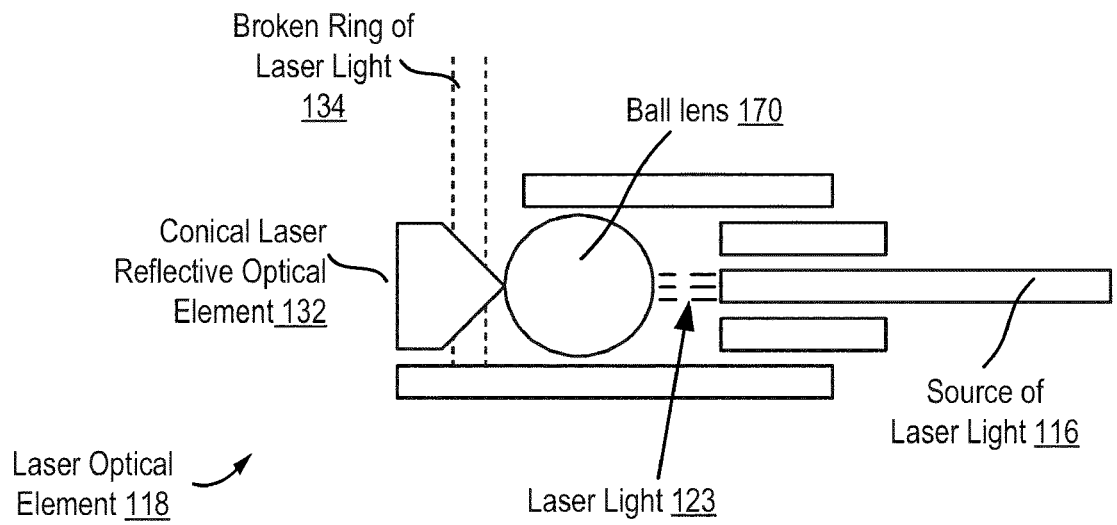
FIGS. 8A and 8B set forth line drawings of a further optical element and a resultant ring of laser light projected from an ear probe having such an optical element.

As mentioned above, otoscanners according to embodiments of the present invention may be configured to project a ring of laser light radially from the tip of the distal end of the ear probe. For further explanation, therefore, FIGS. 8A and 8B set forth line drawings of an optical element (118) useful in scanners according to embodiments of the present invention and a resultant ring of laser light (134) projected from an ear probe having such an optical element. The laser optical element (118) of FIG. 8A includes a conical laser-reflective optical element (132). In the example of FIG. 8A the laser light source (116) and the conical laser-reflecting optical element (132) are configured so that the conical laser-reflecting optical element (132), when illuminated by the laser light source (116), projects a broken ring (134) of laser light upon an interior surface of the ear when the ear probe is positioned in the ear. In the example of FIGS. 6A and 6B, laser light from the laser light source (116) is focused by a ball lens (170) onto the conical laser reflective optical element (132). The conical laser reflective optical element (132) reflects the laser light into a ring of laser light (134) as illustrated in FIGS. 8A and 8B.

Figure 8B:
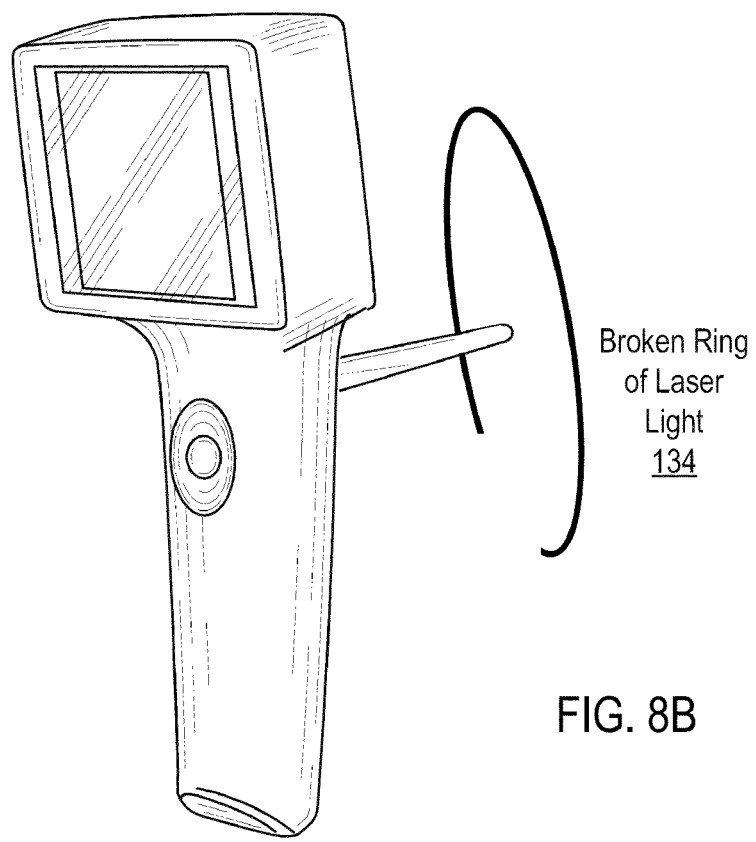

In the examples of FIGS. 8A and 8B the ring of laser light is broken because the conical laser reflective optical element (132) is mounted in a fashion that blocks a portion of the laser light reflected by the optical element. In alternate embodiments, however, the ring of laser light reflected by the conical laser reflective optical element (132) is unbroken as will occur to those of skill in the art.

Figure 9:
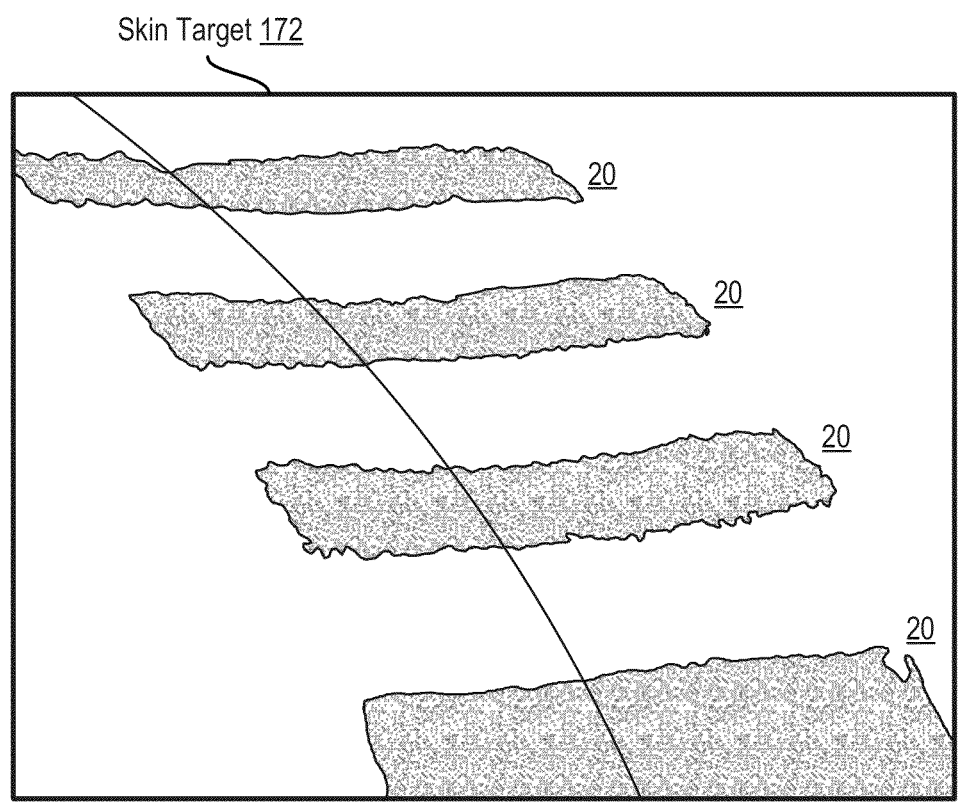
FIG. 9 illustrates a skin target with partial lateral portions of rings of laser light projected thereon.

Referring to FIG. 9, a skin target is shown with partial lateral portions 20 of rings of laser light projected thereon for the purpose of determining how the laser light will project upon skin and its location be marked. A perpendicular section of one of the lateral portions, as shown in FIG. 10, illustrates the fact that the reflected laser light intensity (y-axis) varies in a bell-curve shape with the thickness (x-axis) of the section. Thus, the partial lateral portion 20 may include an edge 22 of the light pattern as well as a ridge 24 of the light pattern. These landmarks may be used to determine the position of the lateral portion 20 in a coordinate system defining an ear space. For example, one of the aforementioned landmarks could be found (such as by a ridge detecting function of a data processor) or an inside edge of the lateral portion or an outside edge of the lateral portion. Or, an average of the inside and outside portions may be used.

Figure 11:
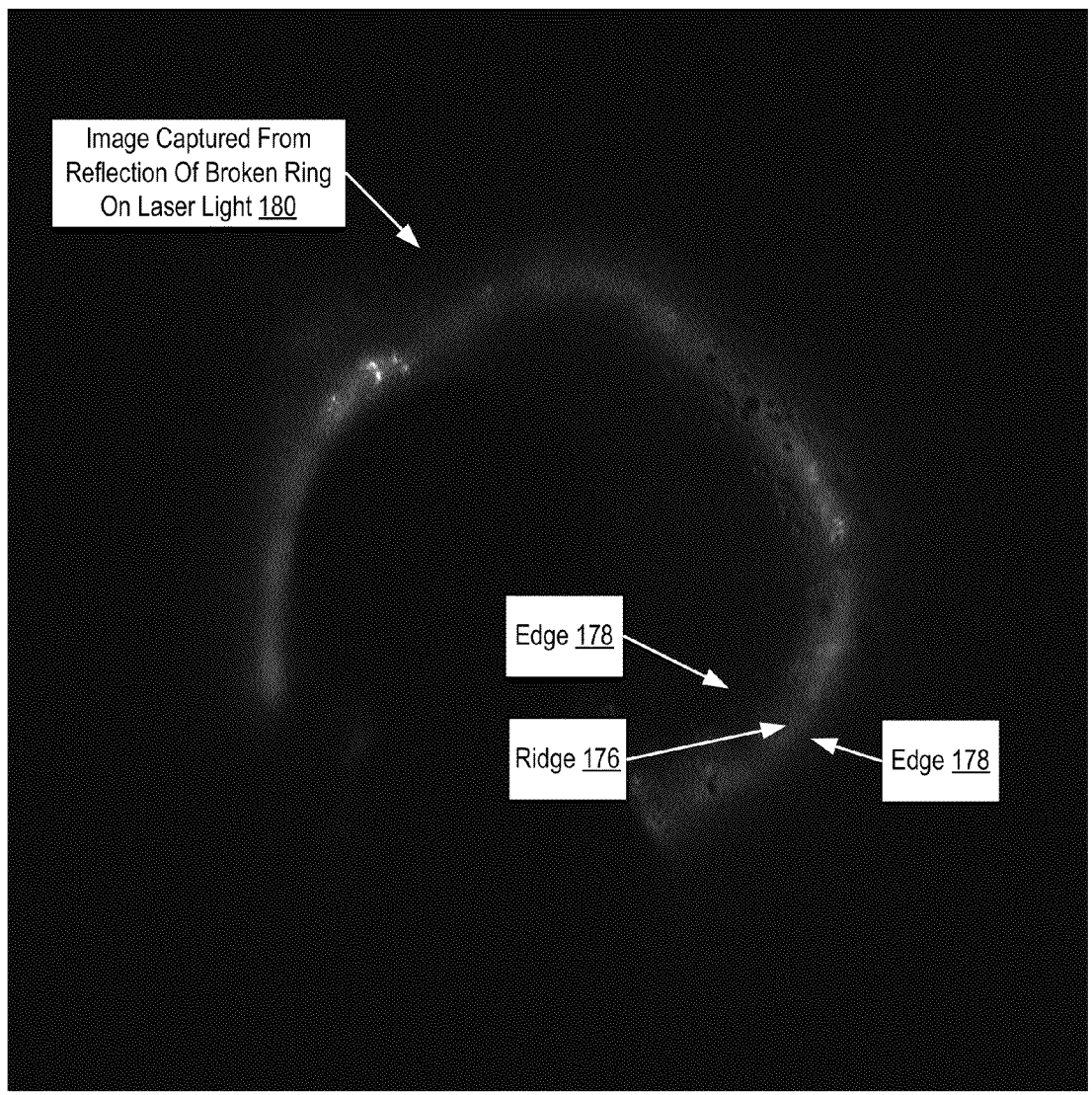
FIG. 11 sets forth an image captured from reflections of laser light reflected from a conical laser reflective optical element.

For further explanation, FIG. 11 sets forth an image captured from reflections of laser light reflected from a conical laser reflective optical element (132) radially from the tip of the ear probe of an otoscanner according to embodiments of the present invention. The captured image of FIG. 11 forms a c-shaped broken ring of pixels of highest intensity. Along the outside and inside of the broken ring (180) are pixels of intensity defining an edge as mentioned above. In between the edges (178) of the broken ring are pixels of higher intensity that define a ridge. The ridge (176) is a collection of ridge points that comprise a set of brightest pixels for the captured 2D image.

Constructing a 3D image of the interior of a scanned ear according to embodiments of the present invention for a sequence of 2D images of the ear such as the image of FIG. 11 includes detecting ridge points for each 2D image. Detecting ridge points in the example of FIG. 11 includes identifying a set of brightest pixels for the 2D image. In the example of FIG. 11, ridge points are detected as a set of brightest pixels along the ridge (176) of the image (180). Detecting ridge points may be carried out by scanning across all pixels in a row on the image sensor and identifying a pixel whose intensity value is greater than the intensity values of pixels on each side. Alternatively, detecting a ridge point may be carried out by identifying range of pixels whose average intensity values are greater than the intensity values of a range of pixels on each side and then selecting one of the pixels in the range of pixels with greater average intensity values. As a further alternative, detecting ridge points can be carried out by taking the brightest pixels from a purposely blurred representation of an image, a technique in which the pixels so selected generally may not be the absolute brightest. An even further alternative way of detecting ridge points is to bisect the full-width half maximum span of a ridge at numerous cross sections along the ridge. Readers will recognize from this description that constructing a 3D image in this example is carried out with some kind of ridge detection. In addition to ridge detection, however, such construction can also be carried out using edge detection, circle detection, shape detection, snakes detection, deconstruction techniques, and in other ways as may occur to those of skill in the art.

Constructing a 3D image of the interior of a scanned ear according to embodiments of the present invention for a sequence of 2D images also includes transforming, in dependence upon a predefined association between each pixel in the image sensor and corresponding points in scanner space, the ridge points to points in scanner space as described with reference to FIG. 11 and transforming, in dependence upon a relationship between an origin of a coordinate system defining scanner space and an origin of another coordinate system defining ear space, the points in scanner space to points in ear space as described with reference to FIG. 13.

Figure 12:
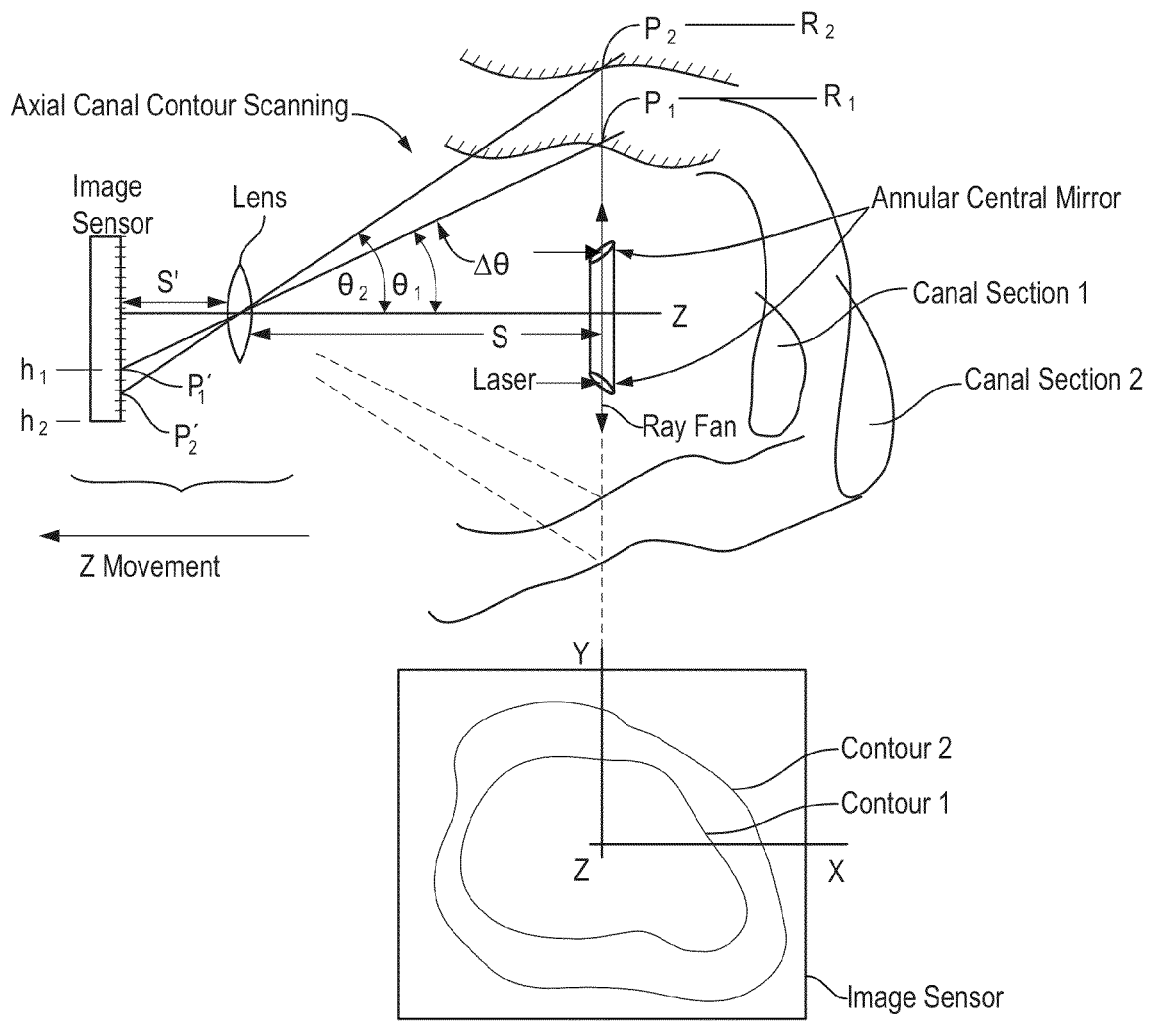
FIG. 12 sets forth a line drawing schematically illustrating transforming ridge points to points in scanner space.

For further explanation, FIG. 12 sets forth a line drawing schematically illustrating transforming, in dependence upon a predefined association between each pixel in the image sensor and corresponding points in scanner space, the ridge points to points in scanner space. FIG. 12 schematically shows an embodiment for calculation of the radial distance of the lateral portion from the optical axis of the probe as implemented by a data processor. The position can be determined by triangulation, as shown in equations 2-8.

$$\frac{h}{S'} \equiv \frac{R}{S} \qquad \text{Equation 2}$$

$$R = \frac{hS}{S'} \qquad \text{Equation 3}$$

$$\frac{S'}{S} = M \qquad \text{Equation 4}$$

$$R = \frac{h}{M} \qquad \text{Equation 5}$$

$$\Delta R = \frac{\Delta h}{M} \qquad \text{Equation 6}$$

$$\theta_{min} = \mathrm{Tan}^{-1}\left(\frac{R_{min}}{S}\right) \qquad \text{Equation 7}$$

$$\theta_{max} = \mathrm{Tan}^{-1}\left(\frac{R_{max}}{S}\right) \qquad \text{Equation 8}$$

In the example of FIG. 12 and in equations 2-8, scanner space is oriented so that its Z axis is centered and fixed as the central axis of an ear probe, looking end-on into the probe, here also referred to as the imaging axis. In this example, therefore, the ratio of the distance R from the imaging axis of a laser-illuminated point to the distance S between the laser plane and the lens is equal to that of the distance h from the center of the image sensor to the distance S' between the image sensor surface and the lens. Magnification M is the ratio of S' and S. When the distances S and S' between the lens and laser plane, and lens to image sensor are known, equations 2-8 can reconstruct the geometry of illuminated points in scanner space. These equations also denote that for a focal surface such as a plane, there is a 1:1 mapping of points in scanner space to pixel locations on the image sensor.

The image sensor 112 may be implemented in complementary-symmetry metallic-oxide-semiconductor ('CMOS') sensor, as a charge-coupled device ('CCD'), or with other sensing technology as may occur to those of skill in the art. A CMOS sensor can be operated in a snapshot readout mode or with a rolling shutter when the scan along the Z-axis is incremented or stepped synchronously to effect a readout of a complete frame. Similar incrementing or stepping may be used for a CCD operated with interlacing scans of image frames.

Constructing a 3D image of the interior of a scanned ear according to embodiments of the present invention also often includes transforming, in dependence upon a relationship between an origin of a coordinate system defining scanner space and an origin of another coordinate system defining ear space, the points in scanner space to points in ear space. For further explanation, therefore, FIG. 13 sets forth a line drawing illustrating an exemplary three-dimensional image (182) of an ear canal constructed from a sequence of 2D images by a data processor. In the example of FIG. 13, each of the 2D images (186) includes a set of transformed ridge points. The transformed ridge points are the result of transforming, in dependence upon a relationship between an origin of a coordinate system defining scanner space and an origin of another coordinate system defining ear space, the points in scanner space to points in ear space as described with reference to FIG. 13. Transforming, in dependence upon a relationship between an origin of a coordinate system defining scanner space and an origin of another coordinate system defining ear space, the points in scanner space to points in ear space may be carried out by as described and illustrated above with reference to FIG. 4.

Figure 14:
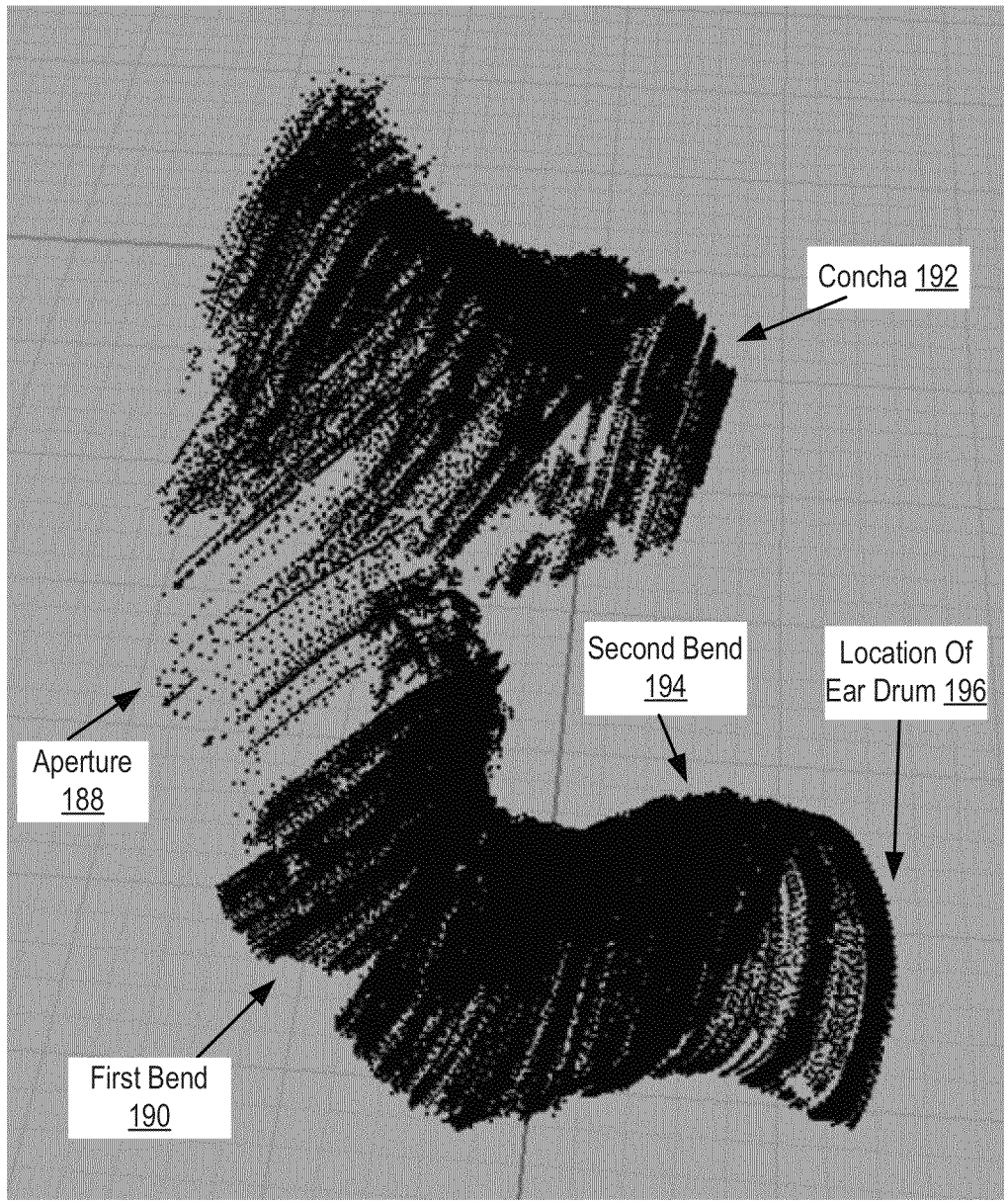
FIG. 14 sets forth a 3D image of a scanned ear created by use of an otoscanner and 3D imaging according to embodiments of the present invention.

For further explanation, FIG. 14 sets forth a 3D image of a scanned ear created by use of an otoscanner and 3D imaging according to embodiments of the present invention. The 3D image of FIG. 14 includes a 3D depiction of the concha (192), the aperture (188) of the ear, the first bend (190) of the ear canal, the second bend of the ear canal and the location of the ear drum (196). The 3D image of FIG. 14 may be used by a manufacturer to provide custom fit hearing aids, custom fit ear buds for personal listening devices, custom fit headphones, and other objects custom fit to the scanned ear and worn in the ear.

The density of portions of the skin making up the ear varies from person to person. The density of portions of the skin making up the ear also varies across the portions of the ear. That is, some people have ears with skin that is more compliant in certain areas of the ear than others. The compliance of the skin of an ear is a factor in determining whether a custom hearing aid, mold, or other object worn in the ear is comfortable to its wearer while still providing a proper fit within the ear. Compliance information may be provided to a manufacturer for use making a comfortable and well fitting hearing aid, mold, or other object worn in the ear. For further explanation, therefore, FIG. 15 sets forth a line drawing of an otoscanner capable of detecting the force with which the ear probe is pressed against a surface of the scanned ear for use in calculating a compliance value as an aid to a manufacturer in making comfortable and well fitting objects worn in the ear. The otoscanner (100) of FIG. 15 is similar to the otoscanner of FIGS. 1 and 2 in that the otoscanner has a body (102), an ear probe (106), video illumination source (120) carrying video illumination from a non-laser light emitter (220), a laser light source for a conical reflective optical element (116a) carrying laser light from a laser (158a) in the body (102) of the otoscanner (100), a laser light source for a diffractive optical lens (116b) carrying light from a laser (158b) in the body (102) of the otoscanner (100) and so on.

Figure 15:
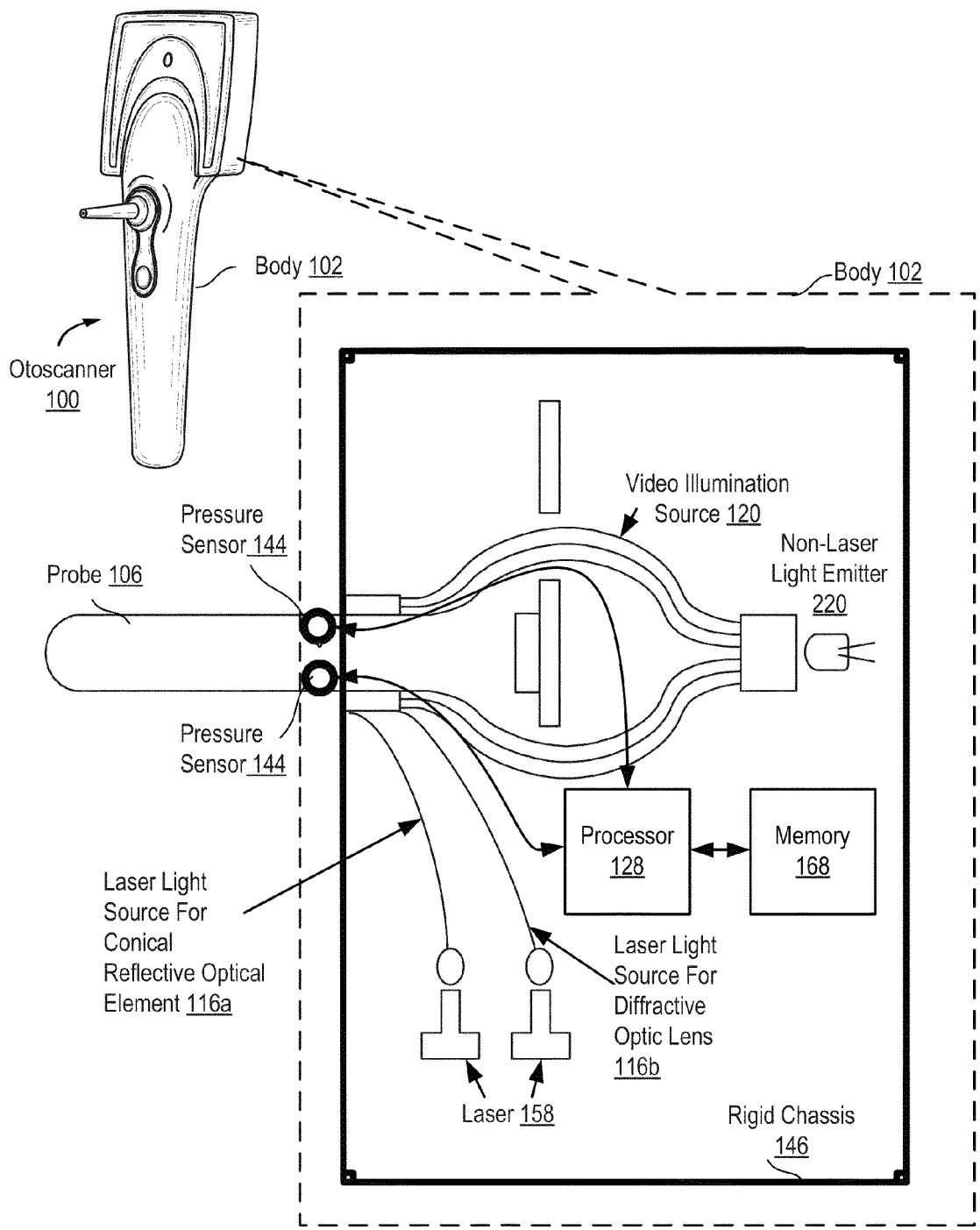
FIG. 15 sets forth a line drawing of an otoscanner capable of detecting the force with which the ear probe is pressed against a surface of the scanned ear for use in calculating a compliance value as an aid to a manufacturer in making comfortable and well fitting objects worn in the ear.

The otoscanner (100) of FIG. 15 differs from the otoscanner of FIGS. 1 and 2 in that the otoscanner body (102) has mounted within it pressure sensors (144) operably coupled to the ear probe (106). In the example of FIG. 15, the pressure sensors (144) are coupled for data communications to the data processor (128) and pressure sensors detect the force with which the ear probe (106) is pressed against a surface of the scanned ear. In some embodiments, the probe is implemented as entirely rigid when scanning. In other embodiments, the probe is implemented as somewhat moveable against pressure sensors for compliance measurements. And some embodiments implement a probe that is alternately both rigid and moveable, providing a locking mechanism that maintains the probe as rigid for optical scanning and allows the probe to move against a pressure sensor when unlocked for ascertaining a compliance value.

The otoscanner (100) is also configured to track positions of the ear probe inferred from reflections of tracking illumination sensed by the tracking illumination sensors (108). The tracked positions are used to identifying the displacement through which the ear probe (106) moves when pressed against the surface of the scanned ear. The data processor (128) of FIG. 15 is further configured so that it functions by calculating a compliance value in dependence upon the detected force and the tracked displacement. The compliance value may be implemented as a single value or range of values dependent upon the detected force and the identified displacement when the probe is pressed against the surface of the scanned ear.

To facilitate the detection of the force when the probe is pressed against the surface of the scanned ear, the otoscanner body (102) has mounted within it pressure sensors (144) operably coupled to the ear probe (106). The tracking sensors (108), the image sensor (112), the probe (106) and lens of the otoscanner (100) of FIG. 15 are all mounted on a rigid chassis (146) that is configured to float within the otoscanner body (102). The pressure sensors (144) are mounted within the otoscanner (100) between the rigid chassis (146) and the otoscanner body (102). The rigid chassis (146) is floated in the body (102) of the otoscanner (100) in that the rigid chassis (146) may move relative to the body (102) of the otoscanner (100) when the probe (106) is pressed against the surface of the ear.

Figure 16:
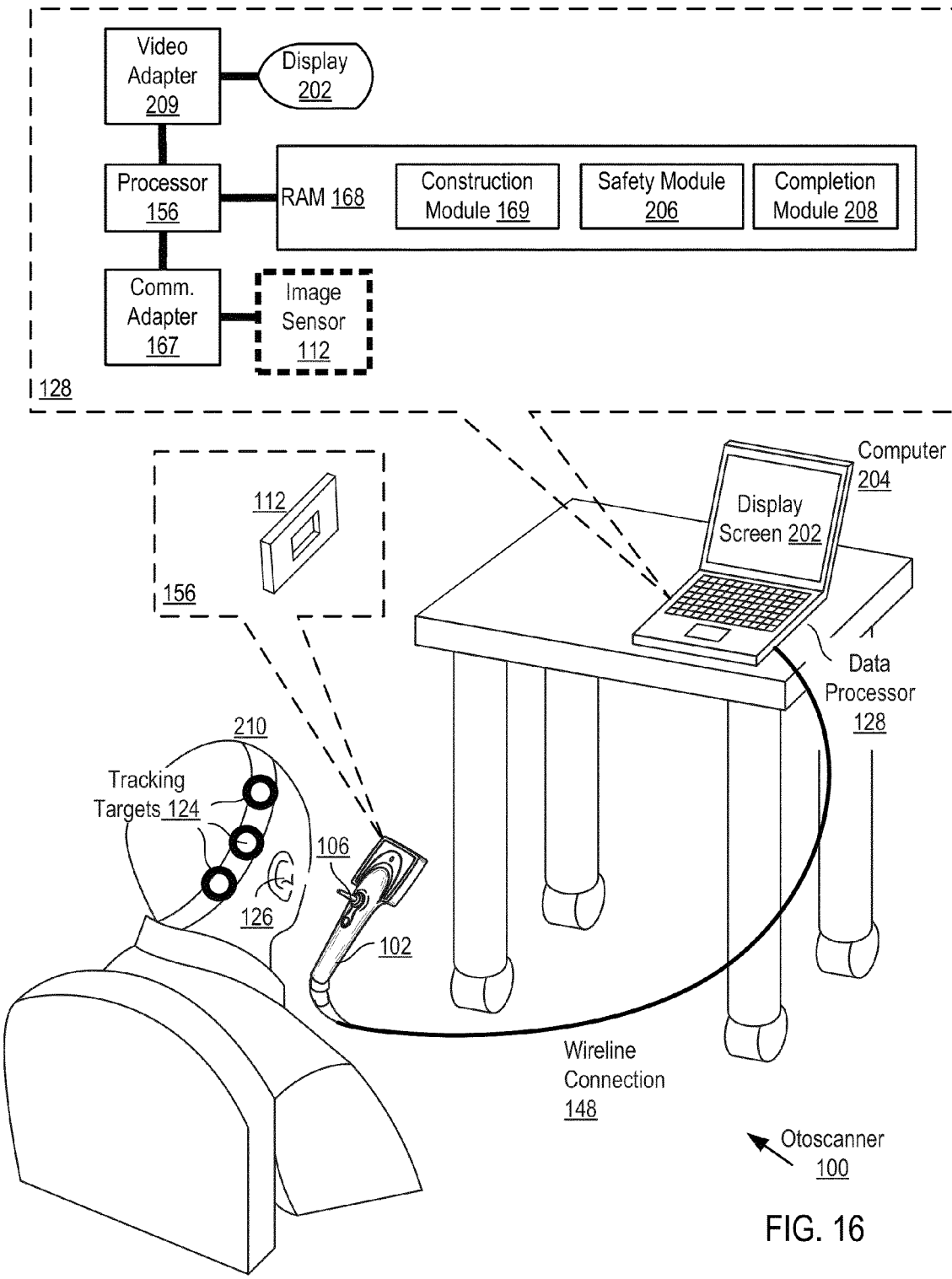
FIG. 16 sets forth a further example otoscanner according to embodiments of the present invention.

In example otoscanners described above, the functionality of the otoscanner is described as residing within the body of the otoscanner. In some embodiments of the present invention, an otoscanner may be configured with a wireline connection to a data processor (128) in a computer (202) available to an operator of the otoscanner. For further explanation, therefore, FIG. 16 sets forth a further example otoscanner according to embodiments of the present invention that includes an otoscanner body (102) with a wireline connection (148) to a data processor (128) implemented in a computer (204). In the example of FIG. 16 the elements of the otoscanner are distributed between the otoscanner body (102) and the computer (204). In the example of FIG. 16, the tracking targets (124) are fixed to a headband worn by the person whose ear (126) is being scanned.

The data processor (128) in the computer (204) of FIG. 16 includes at least one computer processor (156) or 'CPU' as well as random access memory (168) ('RAM') which is connected through a high speed memory bus and bus adapter to processor the (156) and to other components of the data processor (128). The data processor (128) of FIG. 16 also includes a communications adapter (167) for data communications with other computers and with the otoscanner body (102) and for data communications with a data communications network. Such data communications may be carried out serially through RS-232 connections, through external buses such as a Universal Serial Bus ('USB'), through data communications networks such as IP data communications networks, and in other ways as will occur to those of skill in the art. Communications adapters implement the hardware level of data communications through which one computer sends data communications to another computer, directly or through a data communications network. The example data processor FIG. 16 includes a video adapter (209), which is an example of an I/O adapter specially designed for graphic output to a display device (202) such as a display screen or computer monitor.

In the example of FIG. 16, the image sensor (112) is illustrated in callout (156) as residing within the otoscanner body as well as being illustrated in callout (128) as residing in the data processor. An image sensor useful in embodiments of the present invention illustrated in FIG. 16 may reside in either location, or as illustrated in callout (156) or in the computer (202) itself.

In the example of FIG. 16, a display screen (202) on the computer (204) may display images of the scanned ear scanned ear illuminated only by non-laser video illumination (120). The display screen (202) on the computer (113) may also display 3D images of the scanned ear constructed in dependence upon a sequence of images captured by the image sensor as the probe is moved in the scanned ear. In such examples images captured by an image sensor (112)

Stored in RAM (168) in the data processor (128) of FIG. 16 is a construction module. A module of computer program instructions for constructing 3D images of the scanned ear in dependence upon a sequence of images captured by the image sensor (112) as the probe is moved in the scanned ear. The construction module (169) is further configured to determine the position of the probe (106) in ear space when the probe is positioned at the aperture of the auditory canal of the scanned ear (126) and setting the position of the probe at the aperture of the auditory canal of the scanned ear as the origin of the coordinate system defining ear space.

Not all hearing aids, molds, or other objects worn in the ear require the same portions of the ear to be scanned. That is, some objects worn in the ear are small, some are large, some are placed deeper in the ear than others, and so on. As such, stored in RAM (168) in the data processor of FIG. 16 is a completion module (206) a module of computer program instructions for determining whether a scan is complete in dependence upon a class, make, and model, of a hearing aid or other objects worn in the ear. The completion module (208) has a database of classes, makes, and models of hearing aids or other objects worn in the ear. The classes, makes, and models identify the proper portions of the ear to be scanned. The completion module is configured to identify from the 3D image of the ear constructed by the construction module (169) whether the 3D image includes scanned portions of the ear required for the manufacture of a particular class, make and model of a hearing aid or other object worn in the ear. The completion module (208) is also configured to determine whether portions of the ear have simply not been scanned at all. Such portions may appear as holes in the 3D image of the ear.

There is a danger to an ear being scanned if a probe or other object is inserted too deeply in the ear. For example, an ear drum may be damaged if it comes into contact with a probe. Also stored in RAM (206), therefore, is a safety module (206), a module of computer program instructions for safety of use of the otoscanner (100) of FIG. 16. The safety module (206) of FIG. 16 has a database of previously recorded statistics describing typical ear sizes according to human demographics such as height weight, age and other statistics of the humans. The safety module (206) also has currently recorded demographic information regarding a person whose ear is being scanned. The safety module infers, from a tracked position of the ear probe (106), previously recorded statistics describing typical ear sizes according to human demographics, and currently recorded demographic information regarding a person whose ear is scanned, the actual present position of the ear probe in relation to at least one part of the scanned ear. The safety module is configured to provide a warning when the probe moves within a predefined distance from the part of the scanned ear. Such a warning may be implemented as a sound emitted from the otoscanner (100), a warning icon on a display screen of the otoscanner (100) or computer, or any other warning that will occur to those of skill in the art.

Those of skill in the art will recognize that the ear is flexible and the shape of the ear changes when the mouth of the person being scanned is open and when it is closed. To facilitate manufacturing a hearing aid, mold or other object worn in the ear in the example of FIG. 16, an operator scans the ear with the otoscanner of FIG. 16 with the mouth open and then with the mouth closed. 3D images of the ear constructed when the mouth is open and also when the mouth is closed may then be used to manufacture a hearing aid, mold, or other object worn in the ear that is comfortable to the wearer when the wearer's mouth is open and when it is closed. The construction module (169) of the data processor (128) of FIG. 16 is therefore configured to construct the 3D image of the scanned ear by constructing the 3D image in dependence upon a sequence of images captured by the image sensor as the probe is moved in the scanned ear with mouth open. The construction module (169) of the data processor (128) of FIG. 16 is also configured to construct the 3D image of the scanned ear by constructing the 3D image in dependence upon a sequence of images captured by the image sensor as the probe is moved in the scanned ear with mouth closed.

Figure 17:
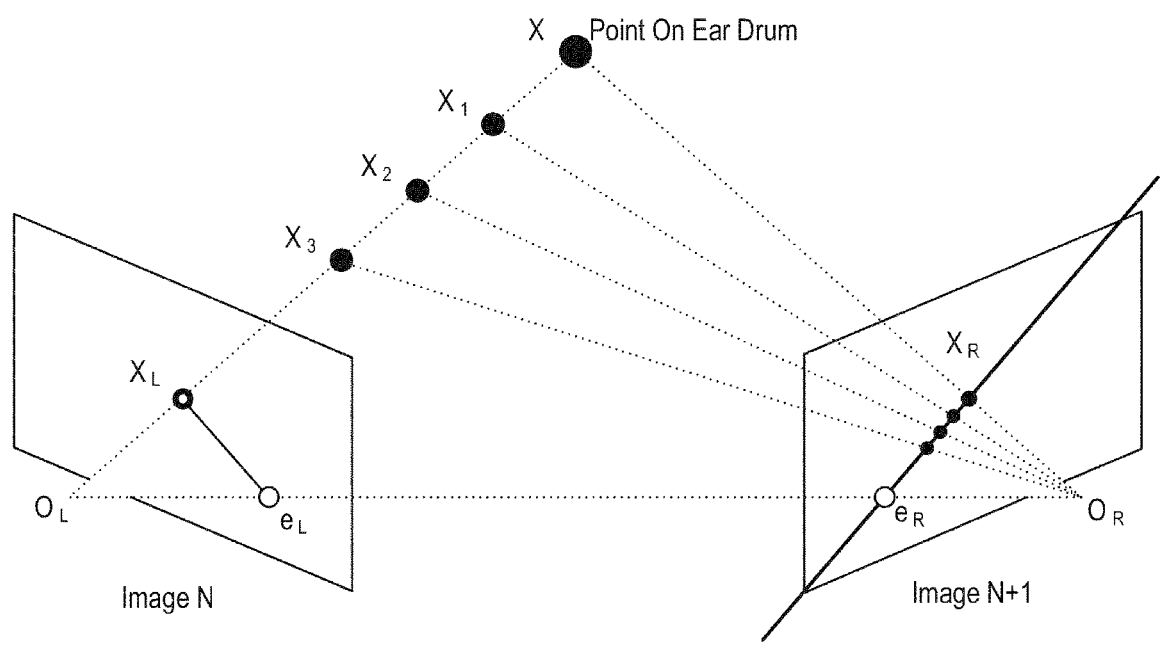
FIG. 17 sets forth a line drawing illustrating a method of determining the location and orientation in ear space of the ear drum of a scanned ear according to a method of structure-from-motion.

The ear drum of a scanned ear is not always in the same place or oriented in the same way relative to an ear. That is, the location and orientation of ear drums differ for different people. Otoscanners according to embodiments of the present invention therefore may be configured to construct a 3D image of the interior of the scanned ear that includes determining the location and orientation in ear space of the ear drum of the scanned ear. For further explanation, FIG. 17 sets forth a line drawing illustrating a method of determining the location and orientation in ear space of the ear drum of a scanned ear according to a method of structure-from-motion. In the example of FIG. 17, the forward field of view (FFOV) as captured through the probe by the otoscanner will see the ear drum in multiple video frames as the probe is moved through the ear. Because the otoscanner tracks the position and orientation of the probe relative to a coordinate system on the head ('ear space'), the otoscanner's data processor can use structure-from-motion to reconstruct the location and direction of the ear drum. Consider one point on the ear drum X that is readily identifiable, such as the umbo, the most depressed part of the concave surface of the ear drum. Referring to the illustration of FIG. 17, consider a point X on the ear drum that is seen on two images N and N+1. On Image N, point X is seen at a pixel location $X_L$, and X falls on a ray $O_L$ $X_L$. From a single image, however, it is not known how far away X is: it could be at X1, X2, X3, etc. Having a second image (Image N+1) allows computation of the distance. In Image N+1, the point on the ear drum X is seen at pixel location $X_R$. It follows that X is on the ray $O_R$-$X_R$. The otoscanner's data processor uses tracking information to transform the direction of these two rays into directions in ear space. Computing the intersection of the rays in ear space yields the location of the point on the ear drum X.

Readers will recognize that the particular structure-from-motion technique just described is not the only way of determining the location and orientation in ear space of the ear drum of the scanned ear. In embodiments, for example, a laser beam provided outside the lenses in a probe is directed parallel to the central axis of the wide angle lens, and the laser produces a dot on the ear drum. In such embodiments, the location of the dot in scope space is determined with structure-from-motion from a single image. In such embodiments, the dot may be somewhat out of focus because the ear drum can be outside of the volume of good focus for the wide angle lens.

Example embodiments of otoscanners have been described with reference to scanning ears. This is for explanation and not for limitation. In fact, otoscanners according to embodiments of the present invention may be used to scan almost any 3D surface of live or inanimate objects both internal and external.

Exemplary embodiments of the present invention are described largely in the context of a fully functional otoscanner and system for scanning an ear. Readers will recognize, however, that aspects of the present invention also may be embodied in a computer program product disposed upon computer readable storage media for use with any suitable data processing system. Such computer readable storage media may be any storage medium for machine-readable information, including magnetic media, optical media, or other suitable media. Examples of such media include magnetic disks in hard drives or diskettes, compact disks for optical drives, magnetic tape, and others as will occur to those of skill in the art. Persons skilled in the art will immediately recognize that any computer system having suitable programming means will be capable of executing aspects of the invention. Persons skilled in the art will recognize also that, although some of the exemplary embodiments described in this specification are oriented to software installed and executing on computer hardware, nevertheless, alternative embodiments implemented as firmware or as hardware are well within the scope of the present invention.

It will be understood from the foregoing description that modifications and changes may be made in various embodiments of the present invention without departing from its true spirit. The descriptions in this specification are for purposes of illustration only and are not to be construed in a limiting sense. The scope of the present invention is limited only by the language of the following claims.

What is claimed is:

1. An otoscanner comprising:
an otoscanner body, the body comprising a hand grip, the body having mounted upon it an ear probe, a tracking illumination emitter, a plurality of tracking illumination sensors, and a display screen, the otoscanner body having mounted within it an image sensor;
the ear probe comprising a wide-angle lens optically coupled to the image sensor, a laser light source, a conical laser-reflective optical element, a diffractive laser optic lens and a source of non-laser video illumination;
the conical laser-reflective optical element and the laser light source configured so that the conical laser-reflecting optical element, when illuminated by the laser light source, projects a broken ring of laser light upon an interior surface of the ear when the ear probe is positioned in the ear;
the diffractive laser optic lens and the laser light source configured so that the diffractive laser optic lens, when illuminated by the laser light source, projects upon an interior surface of the ear a fan of laser light at a predetermined angle with respect to a front surface of the diffractive laser optic lens when the ear probe is positioned in the ear;
the plurality of tracking illumination sensors disposed upon the otoscanner body so as to sense reflections of tracking illumination emitted from the tracking illumination emitter and reflected from tracking targets configured to be installed at positions that are fixed relative to the scanned ear;
the display screen coupled for data communications to the image sensor, the display screen configured for displaying images of the scanned ear, and
the image sensor coupled for data communications to a data processor, with the data processor configured to construct, in dependence upon a sequence of images captured when the scanned ear is illuminated by laser light and tracked positions of the ear probe inferred from reflections of tracking illumination sensed by the tracking illumination sensors, a 3D image of the interior of the scanned ear.

2. The otoscanner of claim 1 wherein the laser light source in the ear probe comprises an optical fiber that conducts laser light to the ear probe from a laser outside the probe.

3. The otoscanner of claim 1 wherein the laser light source comprises a laser mounted in the probe.

4. The otoscanner of claim 1 wherein:
the tracking targets comprise retroreflectors; and the tracking illumination emitter is mounted on the otoscanner body.

5. The otoscanner of claim 1 wherein the tracking illumination is infrared.

6. The otoscanner of claim 1 wherein the data processor is configured such that constructing a 3D image of the interior of a scanned ear further comprises, for a sequence from the image sensor of 2D images of the ear taken when the ear is illuminated by a broken ring of laser light from the ear probe:
   detecting ridge points for each 2D image, the detecting further comprising identifying a set of brightest pixels for each 2D image, each set depicting a c-shaped broken ring of laser light reflecting from a surface of the scanned ear;
   transforming, in dependence upon a predefined association between each pixel in the image sensor and corresponding points in scanner space, the ridge points to points in scanner space; and
   transforming, in dependence upon a relationship between an origin of a coordinate system defining scanner space and an origin of another coordinate system defining ear space, the points in scanner space to points in ear space.

7. The otoscanner of claim 1 wherein the display screen configured for displaying images of the scanned ear further comprises the display screen configured for displaying video images from the image sensor of the scanned ear illuminated only by non-laser video illumination.

8. The otoscanner of claim 1 wherein:
   the otoscanner further comprises the display screen coupled for data communications to the data processor; and
   the display screen configured for displaying images of the scanned ear further comprises the display screen configured for displaying the 3D image of the interior of the scanned ear.

9. The otoscanner of claim 1 wherein:
   the otoscanner body has mounted within it pressure sensors operably coupled to the ear probe and coupled for data communications to the data processor, the pressure sensors configured for detecting the force with which the ear probe is pressed against a surface of the scanned ear.

10. The otoscanner of claim 1 wherein the data processor is further configured to function by:
    determining a position of the probe in ear space when the probe is positioned at the aperture of the auditory canal of the scanned ear; and
    setting the position of the probe at the aperture of the auditory canal of the scanned ear as an origin of a coordinate system defining ear space.

11. The otoscanner of claim 1 wherein constructing the 3D image further comprises constructing the 3D image in dependence upon a sequence of images captured by the image sensor as the probe is moved in the scanned ear.

12. The otoscanner of claim 1 wherein the data processor is configured such that constructing the 3D image further comprises constructing the 3D image in dependence upon a sequence of images captured by the image sensor as the probe is moved in the scanned ear with mouth open.

13. The otoscanner of claim 1 wherein the data processor is configured such that constructing the 3D image further comprises constructing the 3D image in dependence upon a sequence of images captured by the image sensor as the probe is moved in the scanned ear with mouth closed.

14. The otoscanner of claim 1 wherein the data processor is further configured to function by determining whether a scan is complete, the determining carried out in dependence upon a class, make, and model, of a hearing aid.

15. The otoscanner of claim 1 wherein the data processor is further configured to function by:
    inferring, from a tracked position of the ear probe, previously recorded statistics describing typical ear sizes according to human demographics, and currently recorded demographic information regarding a person whose ear is scanned, an actual present position of the ear probe in relation to at least one part of the scanned ear; and
    providing a warning when the probe moves within a predefined distance from the part of the scanned ear.

16. The otoscanner of claim 1 wherein the data processor is configured such that constructing a 3D image of the interior of the scanned ear further comprises determining the location and orientation in ear space of the ear drum of the scanned ear.

* * * * *